(12) United States Patent
Trouet et al.

(10) Patent No.: US 7,893,023 B2
(45) Date of Patent: *Feb. 22, 2011

(54) PRODRUGS ACTIVATED BY PLASMIN AND THEIR USE IN CANCER CHEMOTHERAPY

(75) Inventors: Andre Trouet, Herentals (BE); Vincent Dubois, Fleurus (BE); Alexandre Passioukov, Brussels (BE)

(73) Assignee: Medarex, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/157,575

(22) Filed: Jun. 11, 2008

(65) Prior Publication Data

US 2009/0076176 A1   Mar. 19, 2009

Related U.S. Application Data

(63) Continuation of application No. 10/362,958, filed as application No. PCT/US01/26476 on Aug. 23, 2001, now Pat. No. 7,402,556.

(60) Provisional application No. 60/227,686, filed on Aug. 24, 2000.

(51) Int. Cl.
    *A61K 38/00* (2006.01)
(52) U.S. Cl. .................................. 514/2; 514/17; 514/18
(58) Field of Classification Search ........................ None
    See application file for complete search history.

(56) References Cited

U.S. PATENT DOCUMENTS

| 4,457,866 | A | * | 7/1984 | Karges et al. ............... 530/329 |
| 4,895,842 | A | * | 1/1990 | Okamoto et al. ......... 514/227.5 |
| 2003/0027757 | A1 | * | 2/2003 | Bertin et al. .................. 514/12 |

OTHER PUBLICATIONS

Ullberg et al, Journal of Infectious Disease, 1992, vol. 166, pp. 1329-1334.*
Sierra and de la Torre, Angewandte Chemie, 2000, vol. 39, pp. 1539-1559.*
Baurain et al (Journal of Medicinal Chemistry, 1980, vol. 23, pp. 1171-1174).*
de Groot et al, Journal of Medicinal Chemistry, 1999, vol, 42, pp. 5277-5283.*
DeGroot et al (Molecular Cancer Therapeutics, 2002, vol. 1, pp. 901-911).*
Lahteenmaki et al, Infection and Immunity, 1995, vol. 63, pp. 3659-3664.*

* cited by examiner

*Primary Examiner*—Karen A Canella
(74) *Attorney, Agent, or Firm*—Nelson Mullins Riley & Scarborough LLP; Jane E. Remillard; Brian C. Trinque

(57) ABSTRACT

The product of the invention is a modified form of a therapeutic agent and comprises a therapeutic agent, an oligopeptide having a plasmin peptide substrate of 2-4 amino acids and mono- or di-peptide linkage, a stabilizing group and, optionally, a linker group. The prodrug is cleavable by plasmin. Also disclosed are methods of making and using the prodrug compounds.

37 Claims, No Drawings

SEQUENCE LISTING

```
<160> NUMBER OF SEQ ID NOS: 8

<210> SEQ ID NO 1
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: The amino acid residues at positions one, two,
      three and four make up a plasmin substrate, the amino acid
```

```
      residues at positions three and four can be absent
<220> FEATURE:
<221> NAME/KEY: MISC_FEATURE
<222> LOCATION: (5)..(6)
<223> OTHER INFO
RMATION: The amino acid residues at positions five and
      six are aliphatic amino acids having a large lateral chain, the
      amino acid residue at the sixth position may be absent

<400> SEQUENCE: 1

Xaa Xaa Xaa Xaa Xaa Xaa
1               5

<210> SEQ ID NO 2
<211> LENGTH: 4
<212> TYPE: PRT
<213> ORGANISM: Artificial sequence
<220> FEATURE:
<223> OTHER INFORMATION: Synthetic

<400> SEQUENCE: 2

Phe Glu Lys Lys
1

<210> SEQ ID NO 3
<211> LENGTH: 4
<212> TYPE: PRT
<213> ORGANISM: Artificial sequence
<220> FEATURE:
<223> OTHER INFORMATION: Synthetic

<400> SEQUENCE: 3

Ile Glu Gly Arg
1

<210> SEQ ID NO 4
<211> LENGTH: 4
<212> TYPE: PRT
<213> ORGANISM: Artificial sequence
<220> FEATURE:
<223> OTHER INFORMATION: Synthetic

<400> SEQUENCE: 4

Leu Lys Leu Leu
1

<210> SEQ ID NO 5
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Ala residue is D-Ala

<400> SEQUENCE: 5

Ala Leu Lys Leu
1

<210> SEQ ID NO 6
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
```

-continued

```
<222> LOCATION: (1)..(1)
<223> OTHER INFORMATION: The Ala residue is D-Ala

<400> SEQUENCE: 6

Ala Leu Lys Leu Leu
1               5

<210> SEQ ID NO 7
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: A Succinyl is attached to the Alanine residue;
      the Ala residue is D-Ala

<400> SEQUENCE: 7

Ala Leu Lys Leu
1

<210> SEQ ID NO 8
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: A Succinyl is attached to the Alanine residue;
      the Ala residue is D-Ala

<400> SEQUENCE: 8

Ala Leu Lys Leu Leu
1               5
```

PRODRUGS ACTIVATED BY PLASMIN AND THEIR USE IN CANCER CHEMOTHERAPY

This application is a continuation of U.S. patent application Ser. No. 10/362,958, filed on Oct. 31, 2003, issuing, which is a 35 U.S.C. §371 national stage filing of International Application No. PCT/US01/26476, filed on Aug. 23, 2001, which claims priority to U.S. Provisional Patent Application No. 60/227,686, filed on Aug. 24, 2000. The contents of each of the foregoing applications are hereby incorporated by reference in their entirety.

TECHNICAL FIELD

The present invention relates to compounds useful as prodrugs that are activated by tumor-secreted enzymes. More particularly, the invention relates to prodrugs having a novel mono- or di-peptide linkage and a plasmin peptide substrate of 2-4 amino acids. Such prodrugs may be used for treatment of disease, especially in cancer chemotherapy.

BACKGROUND

Many therapeutic agents, such as anthracyclines and vinca alkaloids, are especially effective in cancer chemotherapy. However, these agents often exhibit acute toxicity in vivo, especially bone marrow and mucosal toxicity, as well as a chronic cardiac toxicity in the case of the anthracyclines and chronic neurological toxicity in the case of the vinca alkaloids. Similarly, methotrexate may be used for the treatment of inflammatory reactions, such as rheumatic diseases, but its high toxicity limits its applications. Development of more and safer specific antitumor agents is desirable for greater effectiveness against tumor cells and a decrease in the number and severity of the side effects of these products (toxicity, destruction of non-tumor cells, etc.). Development of more specific anti-inflammatory agents is also desirable.

The search for more selective anticancer agents has been extremely active for many decades, the dose limiting toxicities (i.e. the undesirable activity of the anticancer agents on normal tissues) being one of the major causes of failures in cancer therapy. Accordingly, the goal has been to improve the specificity of anti-tumor agents for increased effectiveness against tumor cells, while decreasing adverse side effects, such as toxicity and the destruction of non-tumor cells.

The focus of research has been on the development of new therapeutic agents which are in the form of prodrugs, compounds that are capable of being converted to drugs (active therapeutic compounds) in vivo by certain chemical or enzymatic modifications of their structure. For purposes of reducing toxicity, this conversion is preferably confined to the site of action or target tissue rather than the circulatory system or non-target tissue. Prodrugs are often characterized by a low stability in blood and serum, due to the presence of enzymes that degrade or activate the prodrugs before the prodrugs reach the desired sites within the patient's body. A desirable class of prodrugs that addresses such problems has been disclosed in Trouet, et al., U.S. Pat. No. 5,962,216 and in Lobl, et al., PCT International Publication No. WO 00/33888, both of which are incorporated herein by reference.

Tripeptide derivatives of anticancer agents such as daunorubicin ("DNR") and doxorubicin ("DOX"), to be used as prodrugs were studied by Chakravarty, et al., *J. Med. Chem.* 26:633-638, 1983 (A); Chakravarty, et al., *J. Med. Chem.* 26:638-644, 1983 (B); and Balajthy, et al., *J. Med. Chem.* 35:3344-3349, 1992. However, none of these approaches has been shown to be successful.

Other work in this area includes Monsigny, et al., *FEBS Letters* 119(1): 181-186, 1980 (DNR); Baurain, et al., U.S. Pat. No. 4,296,105 (DNR); Baurain, et al., *J. Med. Chem.* 23:1171-1174, 1980 (DNR); Masquelier, et al., *J. Med. Chem.* 23:1166-1170, 1980 (DNR); and de Groot, et al., *J. Med. Chem.* 42:5277-5283, 1999 (DNR and DOX), which all describe prodrugs comprising a carrier linked to the drug via a peptide arm. Typically, these references describe a peptide arm, linked via its free carboxyl function to the free amine function of derivatives of anthracyclines such as DNR. In addition, the arm of these prodrugs can be linked via its free amine function to a carrier consisting of a macromolecule (protein such as BSA, immunoglobulins, etc.) which permits the selective endocytosis of the prodrug by target cells.

However, in spite of the advances in the art, there continues to be a need for the development of useful prodrug compounds and methods of making such prodrugs. Prodrugs that display a high specificity of action, reduced toxicity, and improved stability in blood relative to known prodrugs of similar structure are particularly desirable. The instant invention addresses those needs.

SUMMARY OF THE INVENTION

One aspect of the invention relates to compounds that are prodrug forms of therapeutic agents with a mono- or di-peptide linkage and a plasmin peptide substrate of 2-4 amino acids (i.e., a dipeptide, tripeptide or tetrapeptide substrate), which in turn, is linked to a stabilizing group. In essence, the prodrug comprises a plasmin-recognizable peptidic sequence linked to one or two aliphatic amino acids having a large lateral chain which aliphatic amino acid is further linked to the drug. These prodrugs display a high specificity of action, reduced toxicity, improved stability in the serum and blood, and exhibit minimal movement into target cells unless activated by a target cell associated enzyme.

In one aspect of the invention, the compound comprises: (1) a therapeutic agent capable of entering a target cell; (2) an oligopeptide having the formula X-Y, where X is a plasmin peptide substrate of 2-4 amino acids and Y is a peptide comprising 1-2 aliphatic amino acids having large lateral chains; (3) a stabilizing group; and (4) optionally, a linker group not cleavable by plasmin; wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide; wherein the stabilizing group hinders cleavage of the oligopeptide by enzymes present in whole blood; and wherein the compound is cleavable by plasmin. In another aspect of the invention, the compound is selectively cleavable by plasmin.

In another aspect of the invention, the oligopeptide has the formula $(AA^x)_m$-$(AA^y)_n$ (SEQ ID NO:1) wherein: $(AA^x)_m$ is a plasmin substrate and each $AA^x$ independently represents an amino acid; each $AA^y$ independently represents an aliphatic amino acid having a large lateral chain, m is an integer from 2-4; and n is an integer from 1-2, said oligopeptide being cleavable by plasmin.

Another aspect of the invention pertains to a pharmaceutical composition comprising these prodrugs and optionally a pharmaceutically acceptable carrier.

Yet another aspect of the invention pertains to compounds comprising a marker useful in the characterization of tumors, for example, diagnosis, progression of the tumor, and assay of the factors secreted by tumor cells. Another aspect of the invention relates to articles of manufacture for diagnosis or conducting assays comprising: (1) a compound comprising (a) a marker, (b) the oligopeptide described above, (c) a stabilizing group, and (d) optionally, a linker group not cleavable by plasmin; and (2) at least one reagent useful in the detection of the marker.

Another aspect of the invention relates to methods of treating a medical condition by administering a prodrug of the invention to a patient in a therapeutically effective amount.

Yet another aspect of the invention pertains to a method for decreasing the toxicity of a therapeutic agent wherein the therapeutic agent is intended for administration to a patient, the method comprising: covalently forming a prodrug by linking the oligopeptide described above to a stabilizing group at a first attachment site of the oligopeptide and directly or indirectly linking the therapeutic agent at a second attachment site of the oligopeptide, whereby the prodrug provides for decreased toxicity of the therapeutic agent when administered to the patient.

DETAILED DESCRIPTION OF THE INVENTION

The invention describes prodrugs that (1) are sufficiently stable in the bloodstream and in the biological fluids, to achieve important concentrations at tumor level in its non-hydrolyzed form; (2) are unable to enter, as such, into either normal or tumoral cells; and (3) are activated extracellularly by proteases secreted by tumor cells and having a hydrolysis rate considerably high to provide the liberation of sufficient quantities of active agent capable of entering cells and reaching its intracellular targets. The prodrugs are activated by plasmin, an enzyme overproduced in the vicinity of a large number of human tumor cells.

Before proceeding with the description of the invention, it may be helpful to set forth the abbreviations used herein.

ABBREVIATIONS

ACN Acetonitrile
B16-B16 B16-B16 melanoma cells
BFS Bovine fetal serum
Boc t-Butyloxycarbonyl
BSA Bovine serum albumin
Bz Benzyl
Cbz Benzyloxycarbonyl
CM Conditioned medium
DBN 1,5 Diazabicyclo[4.3.0]non-5-ene
DBO 1,4 Diazabicyclo[2.2.2]octane
DBU 1,8-Diazabicyclo[5.4.0]undec-7-ene
DCC N,N'Dicyclohexylcarbodiimide
DCM Dichloromethane
DIC N,N'-Diisopropylcarbodiimide
DIPEA Diisopropylethylamine
DMEM Dulbecco's Modified Eagle Medium
DMF Dimethylformamide
DNR Daunorubicin
DMSO Dimethylsulfoxide
DOX Doxorubicin
EDTA Ethylenediaminetetraacetic acid, tetrasodium salt
EtOH Ethanol
Et$_2$O Diethyl ether
Fmoc 9-Fluorenylmethyloxycarbonyl
HATU O-(7-Azabenzotrazol-1-yl)-1,1,3,3-tetramethyluronium-hexafluorophosphate
HBTU 2-(1H-Benzotriazole-1-yl) 1,1,3,3-tetramethyluronium-hexafluorophosphate
HOBT N-Hydroxybenzotriazole
HPLC High pressure liquid chromatography
KSCN Potassium isothiocyanate
Me Methyl
MeOH Methanol
MeOSucc Methyl hemisuccinate or methyl hemisuccinyl
NaOAc Sodium acetate
NMP N-methylpyrrolidone
NMR Nuclear magnetic resonance
OSu the N-hydroxysuccinimide ester
PAM resin 4-hydroxymethylphenylacetamidomethyl
PBS Phosphate buffered saline: NaH$_2$PO$_4$ 2.8 mM, NaHPO$_4$ 7.2 mM, NaCl 150 mM, pH 7.4
PEG Polyethylene glycol
PyBOP benzotriazole-1-yl-oxy-tris-pyrrolidino-phosphonium hexafluorophosphate
Pyg Pyroglutamic acid
RT Room temperature
SPPS Merrifield solid phase peptide synthesis method
Succ Succinyl Acid/Succinyl
tBu tert-Butyl
TCE trichloroethyl
TEA Triethylamine
TES buffer Tris-HCl 50 mM, EDTA 50 mM in H$_2$O, pH 8.0
TFA Trifluororoacetic acid
THF Tetrahydrofuran
TLC Thin Layer Chromatography
Tos p-Toluenesulfonyl Prodrugs The prodrug of the invention is a modified form of a therapeutic agent and comprises several portions, including: (1) a therapeutic agent; (2) an oligopeptide; (3) a stabilizing group; and (4) optionally, a linker group. Each of the portions of the prodrug are discussed in greater detail below. A typical orientation of a prodrug of the invention is as follows:

(stabilizing group)-(oligopeptide)-(optional linker group)-(therapeutic agent)

The stabilizing group is directly linked to the oligopeptide at a first attachment site of the oligopeptide. The oligopeptide is directly or indirectly linked to the therapeutic agent at a second attachment site of the oligopeptide. If the oligopeptide and the therapeutic agent are indirectly linked, then a linker group is present.

As used herein, the term "direct" linkage of two portions of the prodrug means a covalent bond exists between the two portions. The stabilizing group and the oligopeptide are directly linked via a covalent chemical bond at a first attachment site of the oligopeptide. Similarly, the oligopeptide and the therapeutic agent can be directly linked by a covalent bond at a second attachment site of the oligopeptide.

As used herein, the term "indirect" linkage of two portions of the prodrug means each of the two portions is covalently bound to a linker group. Accordingly, in an alternative embodiment, the stabilizing group and the oligopeptide are directly linked via a covalent chemical bond at a first attachment site of the oligopeptide and the oligopeptide and the therapeutic agent are indirectly linked by a linker group at a second attachment site of the oligopeptide.

The first attachment site of the oligopeptide is typically at the N-terminus and the second attachment site is typically at the C-terminus. However, in an alternative embodiment, the orientation of the prodrug may be reversed so that the stabilizing group is directly linked to the C-terminus of the oligopeptide and the therapeutic agent is directly or indirectly linked to the N-terminus of the oligopeptide. Thus, in the alternative embodiment, the first attachment site may be the C-terminus of the oligopeptide and the second attachment site of the oligopeptide may be the N-terminus of the oligopeptide. The alternative embodiment of the invention functions in the same manner as does the primary embodiment.

The oligopeptide portion of the prodrug of the invention comprises two regions: a plasmin peptide substrate and a 1-2 aliphatic amino acid linkage. In order for the prodrug to be effective, the prodrug typically undergoes in vivo modification and an active portion, i.e., a transport-competent portion, of the prodrug enters the target cell. A first cleavage within the oligopeptide portion of the prodrug may leave an active or transport-competent portion of the prodrug as one of the cleavage products. Alternatively, further cleavage by one or more peptidases may be required to result in a portion of the prodrug that is capable of entering the cell. The active portion of the prodrug has at least the therapeutic agent and is that part of the prodrug that can enter the target cell to exert a therapeutic effect directly or upon further conversion within the target cell. Thus, the compound has an active portion, and the active portion is more capable of entering the target cell after cleavage by plasmin, an enzyme associated with the target cell, than prior to cleavage by plasmin.

The structures of the stabilizing group and oligopeptide are selected to limit clearance and metabolism of the prodrug by enzymes that may be present in blood or non-target tissue and are further selected to limit transport of the prodrug into the cells. The stabilizing group blocks degradation of the prodrug and may act in providing preferable charge or other physical characteristics of the prodrug. The amino acid sequence of the oligopeptide is designed to ensure specific cleavage by plasmin.

It is desirable to make a therapeutic agent, especially an antitumor and/or anti-inflammatory therapeutic agent, inactive by modification of the therapeutic agent to a prodrug form. According to the invention, the target cells are usually tumor cells or cells participating in inflammatory reactions, especially those associated with rheumatic diseases, such as macrophages, neutrophils, and monocytes. Modification of the therapeutic agent to a prodrug form also reduces some of the side effects of the therapeutic agents.

In the target cell, the therapeutic agent (optionally attached to one or two aliphatic amino acids and possibly also a linker group) acts either directly on its specific intracellular action site or, after a modification by intracellular proteases, kills the target cell or blocks its proliferation. Since normal cells do not activate plasminogen into plasmin in vivo as is seen with tumor cells, the prodrugs of the invention are maintained inactive and do not enter the normal cells or do so to a relatively minor extent.

The prodrug is administered to the patient, carried through the blood stream in a stable form, and when in the vicinity of a target cell, is acted upon by plasmin. Since the enzyme activity is only minimally present within the extracellular vicinity of normal cells, the prodrug is maintained and its active portion (including the therapeutic agent) gains entry into the normal cells only minimally. In the vicinity of tumor or other target cells, however, the presence of plasmin in the local environment allows for cleavage of the prodrug. Once the prodrug is cleaved extracellularly, the transport-competent or active portion gains entry into the target cell. Once within the target cell, it may be further modified to provide therapeutic effect, such as by killing the target cell or blocking its proliferation. While a portion of the prodrug may occasionally gain access to, and possibly harm normal cells, the transport-competent portion of the drug is freed primarily in the vicinity of target cells. Thus, toxicity to normal cells is minimized.

This process is particularly useful for, and is designed for, target cell destruction when the target tissue excretes an enzyme or other factor that is not secreted by normal cells. Here "normal cells" means non-target cells that would be encountered by the prodrug upon administration of the prodrug in the manner appropriate for its intended use. Since normal cells liberate little or none of the target-cell enzyme(s) that are responsible for cleaving the bond that links the active portion (including the therapeutic agent) of the prodrug from the remainder of the prodrug in vivo, the compound of the invention is maintained inactive and does not enter the normal cells.

As described in greater detail below, the prodrugs of the invention are compounds comprising:

(1) a therapeutic agent capable of entering a target cell;

(2) an oligopeptide having the formula X-Y, where X is a plasmin peptide substrate of 2-4 amino acids and Y is a peptide comprising 1-2 aliphatic amino acids having large lateral chains;

(3) a stabilizing group; and (4) optionally, a linker group not cleavable by plasmin;

wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide;

wherein the stabilizing group hinders cleavage of the oligopeptide by enzymes present in whole blood; and wherein the compound is cleavable by plasmin.

As used herein, "cleavable by" means cleavable under physiological conditions.

The oligopeptide can also be described as: $(AA^x)_m$-$(AA^y)_n$ (SEQ ID NO:1) wherein: $(AA^x)_m$ is a plasmin substrate and each $AA^x$ independently represents an amino acid; each $AA^y$ independently represents an aliphatic amino acid having a large lateral chain; m is an integer from 2-4; and n is an integer from 1-2.

Target Cell Associated Enzyme: Plasmin

The prodrugs of the invention are designed to take advantage of preferential activation through interaction with plasmin, an enzyme associated with the target cell, at or near the site targeted within the body of the patient. The involvement of proteases, such as the plasminogen activation system, in the cascade of events leading to the metastatic spread of cancer cells has been well documented. Based on the involvement of this system in malignancy, and on the concept and technology previously developed in the work on other prodrugs (Trouet, et al., U.S. Pat. No. 5,962,216), several attempts were made to develop prodrugs of anticancer agents that could be activated by plasmin. The anthracycline daunorubicin ("DNR") was used as a model drug and several peptidic sequences were linked via their carboxyl end to the amino group of the sugar moiety of the drug.

Based on previous experimental data, it was known that sequences of four amino acid residues would allow the prodrug to be sufficiently stable in the bloodstream and in the biological fluids. The peptide sequences used were selected according to the known substrate specificity of plasmin as described in the literature. In particular, plasmin is a serine protease with trypsin-like specificity, cleaving lysine and arginine bonds. In addition, it is known that plasmin specifically recognizes some peptidic sequences (Lottenberg, et al., *Meth. Enzymol.* 80:341-361, 1981), and among them D-Alanyl-Leucyl-Lysyl-M and D-Val-Leu-Lys-M, cleaving the peptide bond between the Lysyl residue and the M marker (Smith, et al., *Thromb. Res.* 17:393, 1980).

As far as plasmin specificity is concerned, several different sequences are possible and have been previously described. Some of these other sequences have been tried for the generation of tripeptide derivatives of anticancer agents to be used as prodrugs, but with very little activity in vivo (Chakravarty, et al. (A), supra; Chakravarty, et al. (B), supra; and Balajthy, et al., supra. These prodrugs were oligopeptidic derivatives of the respective anticancer agent, and were designed in such a way that plasmin action on these derivatives should have regenerated the active compound at the tumor level. However, in the case of anthracyclines (DOX, DNR, etc), these tripeptidic derivatives proved to be very poor substrates for plasmin (D-Val-Leu-Lys-DOX described in Chakravarty, et al. (A), supra and Chakravarty, et al. (B), supra;). More recently, a self-immolative spacer was placed between the tripeptide D-Ala-Phe-Lys to provide prodrugs with relative selectivity to plasmin (de Groot, et al., supra).

In the instant invention, one or two aliphatic amino acids with large lateral side chains, preferably are intercalated between the plasmin substrate sequences described in the art and an agent of interest. In the instant invention, plasmin substrate-Leu-DNR was evaluated, and the effect of modifications of the first N-terminal residue on blood stability was checked. A potentially interesting plasmin-activated prodrug was then selected on the basis of its stability in whole blood and of its degradation into Leu-DNR by purified plasmin as well as by media conditioned by a human breast cancer cell line (MCF-7/6). The structure of this prodrug was D-Ala-Leu-Lys-Leu-DNR (Compound I, DNR). An additional Leu residue was added to provide the prodrug D-Ala-Leu-Lys-Leu-Leu-DNR (Compound II, DNR).

It is understood that other amino acid sequences specifically recognized by plasmin can also be coupled to therapeutic agents in a way to assure an efficient dipeptidyl-agent liberation.

A distinctive feature of the instant invention is the introduction of this single or double aliphatic residue between the specific peptide sequence cleaved off by plasmin and the therapeutic agent, creating a spacer linkage between the enzyme substrate and the drug. It is believed that this spacer linkage facilitates the access of plasmin to the bond that is cleaved. The aliphatic amino acid has a large lateral side chain is preferably a leucine residue. However, other aliphatic amino-acids having a large lateral chain are also suited for use in the invention. These include by way of example and not limitation, phenylalanine, isoleucine and valine residues.

While demonstrated for the drug DNR, the plasmin-sensitive peptide sequences of the invention (D-Ala-Leu-Lys-Leu- and D-Ala-Leu-Lys-Leu-Leu, for example) can be used not only to prepare DNR prodrugs, but also prodrugs of a series of other anticancer agents, as well as of several chemo- or radiosensitizers. In addition, another aspect of the invention involves using this sequence, not only with drugs that are currently used clinically, but also with agents that cannot be used because of their prohibitive toxicity. Therefore, another aspect of the invention relates to a method of significantly reducing the toxicity of an agent while conserving or enhancing its activity.

Stabilizing Group

An important portion of the prodrug is the stabilizing group, which serves to protect the prodrug compound from cleavage in circulating blood when it is administered to the patient and allows the prodrug to reach the vicinity of the target cell relatively intact. The stabilizing group protects the prodrug from cleavage by proteinases and peptidases present in blood, blood serum, and normal tissue. Particularly, in the preferred embodiment, where the stabilizing group caps the N-terminus of the oligopeptide, and is therefore sometimes referred to as an N-cap or N-block, the stabilizing group serves to ward against peptidases to which the prodrug may otherwise be susceptible.

Ideally, the stabilizing group is useful in the prodrug of the invention if it serves to protect the prodrug from degradation, i.e., cleavage, when tested by storage of the prodrug compound in human blood at 37° C. for 2 hours and results in less than 20%, preferably less than 2%, cleavage of the prodrug by the enzymes present in the human blood under the given assay conditions.

More particularly, the stabilizing group can be one of the following:

(1) a non-amino acid group, i.e., a group other than an amino acid; or (2) an amino acid that is preferably either (i) a non-genetically-encoded amino acid having four or more carbons or (ii) aspartic acid or glutamic acid attached to the N-terminus of the oligopeptide at the β-carboxyl group of aspartic acid or the γ-carboxyl group of glutamic acid; or (3) a non-amino acid group covalently linked to an amino acid that is preferably either (i) a non-genetically-encoded amino acid having four or more carbons or (ii) aspartic acid or glutamic acid attached to the N-terminus of the oligopeptide at the β-carboxyl group of aspartic acid or the γ-carboxyl group of glutamic acid.

Examples of non-amino acid groups include, by way of example and not limitation, dicarboxylic (or a higher order carboxylic) acid or a pharmaceutically acceptable salt thereof. Since chemical radicals having more than two carboxylic acids are also acceptable as part of the prodrug, the end group having dicarboxylic (or higher order carboxylic) acids is an exemplary N-cap. The N-cap may thus be a monoamide derivative of a chemical radical containing two or more carboxylic acids where the amide is attached onto the amino terminus of the peptide and the remaining carboxylic acids are free and uncoupled. For this purpose, the N-cap is preferably succinic acid, methyl hemisuccinate, adipic acid, glutaric acid, or phthalic acid, with adipic acid and succinic acid being most preferred. Other examples of useful N-caps in the prodrug compound of the invention include diglycolic acid, fumaric acid, naphthalene dicarboxylic acid, pyroglutamic acid, acetic acid, 1 or 2, naphthylcarboxylic acid, 1,8-naphthyl dicarboxylic acid, aconitic acid, carboxycinnamic acid, triazole dicarboxylic acid, gluconic acid, 4-carboxyphenyl boronic acid, PEG and $(PEG)_n$-analogs, butane disulfonic acid, and maleic acid. Other non-amino acid stabilizing groups include BSA, Boc, Bz and Cbz, Tos, wheat germ agglutinin and succinylated wheat germ agglutinin and dextran.

Suitable amino acid stabilizing groups include, by way of illustration and not limitation, βAla (linked via its carboxyl function to the oligopeptide), α-methyl-Ala, D-Val, D-Ala, D-Phe, D-Ile, D-Pro and poly[$N^5$-(2-hydroxyethyl)-L-glutamine], with β-Ala, α-methyl-Ala and D-Ala being preferred.

Suitable stabilizing groups that are made up of a non-amino acid group covalently linked to an amino acid, include by way of illustration and not limitation, Succ-βAla, Succ-α-methyl-Ala and Succ-D-Ala.

Many cytotoxic compounds inherently have low solubility. Positively charged anthracyclines for example may form aggregates at high concentration and these aggregates may induce intravenous coagulation when the aggregates are administered intravenously. Since many oligopeptides have exposed, positively-charged amino termini at physiological pH, these aggregates may form a polypositively charged surface in vivo and induce a coagulation cascade within a few minutes of administration. This has the potential for rendering any positively charged prodrugs that form aggregates unsuitable for therapeutic use.

One way of addressing such a potentially dangerous obstacle is to utilize the stabilizing group on the peptide chain N-terminus of a negatively charged or a neutral functionality. For example, the use of succinyl as a stabilizing group on the prodrug alleviates the prodrug's acute toxicity. This solves an important problem in the use of peptide prodrugs as practical therapies for intravenous use in humans.

Oligopeptide

Oligopeptides are generally defined as polypeptides of short length. An oligopeptide useful in the prodrug of the invention is 3-6 amino acids in length, however.

As indicated above, the oligopeptide has the formula X-Y, where X is a plasmin peptide substrate of 2-4 amino acids and Y is a peptide comprising 1-2 aliphatic amino acids having large lateral chains. This can also be stated as the formula or sequence (shown in the typical amino-terminus to carboxy-terminus orientation): $(AA^x)_m$-$(AA^y)_n$ (SEQ ID NO:1) wherein: $(AA^x)_m$ is a plasmin substrate and each $AA^x$ independently is an amino acid; each $AA^y$ independently represents an aliphatic amino acid having a large lateral chain; m is an integer from 2-4; and n is an integer from 1-2.

The amino acid sequence of protease cleavage sites is conventionally denoted as $H_2N$— . . . -P3-P2-P1-P1'-P2'-P3'- . . . —COOH, where the bond cleaved is between amino acids P1 and P1' (Schlecter, et al., *Biochem. Biophys. Res. comm.* 27:157-162, 1967). Plasmin is a protease with specificity for arginine or lysine at the P1 position, with lysine being preferred. In several known plasmin substrates, P2 is a hydrophobic amino acid while P3 shows no apparent specificity. Accordingly, sequences containing "-amino acid P3-hydrophobic amino acid P2-lysine or arginine P1-" are expected to be good plasmin substrates (Carl, et al., *Proc. Natl. Acad. Sci. USA* 77(4):2224-2228 (1980).

Therefore, X-Y in its largest embodiment, corresponds to a position sequence -P4-P3-P2-P1-P1'-P2'-, where plasmin cleaves between the P1 and P1' positions. The "X" plasmin peptide substrate of 2-4 amino acids corresponds to the -P4-P3-P2-P1-section, while the "Y" 1-2 aliphatic amino acid peptide corresponds to the -P1'-P2'-section. Despite the short length of the oligopeptide portion of the prodrug herein described, the selectivity for cleavage of the prodrug by plasmin is maintained.

Preferred Amino Acids

Unless otherwise indicated, all amino acids described herein are in the L configuration.

The following are examples of plasmin substrates suitable for use as the "X" plasmin peptide substrate of the oligopeptide. It is understood that this table is intended to be illustrative and not limiting in any manner.

TABLE 1

| $AA^{x4}$ (P4) | $AA^{x3}$ (P3) | $AA^{x2}$ (P2) | $AA^{x1}$ (P1) | SEQ ID NO: (if required) |
|---|---|---|---|---|
| | | Leu | Lys | |
| | Val | Leu | Lys | |
| | | Phe | Lys | |
| | Ala | Phe | Lys | |
| | | Ala | Lys | |
| | Ala | Ala | Lys | |
| | Leu | Lys | Lys | |
| | Glu | Lys | Lys | |
| Phe | Glu | Lys | Lys | SEQ ID NO: 2 |
| | | Glu | Lys | |
| | Phe | Glu | Lys | |
| | Ile | Glu | Lys | |
| | Gly | Pro | Lys | |
| | | Gly | Arg | |
| | Gly | Gly | Arg | |
| | Val | Gly | Arg | |
| Ile | Glu | Gly | Arg | SEQ ID NO: 3 |
| | | Pro | Arg | |
| | Gly | Pro | Arg | |
| | Phe | Val | Arg | |
| | | Leu | Arg | |
| | | Phe | Arg | |
| | Pro | Phe | Arg | |

Although many amino acids may be present in the oligopeptide portion of the prodrug, certain amino acids are preferred:

Suitable amino acid residues for the P4 or $AA^{x4}$ position, include Ile and Phe residues.

Suitable amino acid residues for the P3 or $AA^{x3}$ position, include Ala, Glu, Gly, Ile, Leu, Phe, Pro and Val residues.

Suitable amino acid residues for the P2 or $AA^{x2}$ position, include Ala, Glu, Gly, Leu, Lys, Phe, Pro and Val residues.

Suitable amino acid residues for the P1 or $AA^{x1}$ position, include arginine or lysine residues.

The following are examples of mono- or dipeptides useful for use as the "Y" portion of the oligopeptide. It is understood that this table is intended to be illustrative and not limiting in any manner. Unless otherwise indicated, all amino acids are in the L configuration.

TABLE 2

| $AA^{y1}$ (P1') | $AA^{y2*}$ (P2')* |
|---|---|
| Leu | — |
| Leu | Leu |

*If absent, then Y comprises one amino acid, $AA^{y1}$.

Suitable aliphatic amino acid residues having a large lateral chain for the P1' or $AA^{y1}$ and the P2' or $AA^{y2}$ position, include Ile, Leu, Phe and Val residues. Leu is the preferred residue.

Some preferred oligopeptides useful in the prodrug of the invention include the following, shown in Table 3:

TABLE 3

| $AA^{x4}$ (P4) | $AA^{x3}$ (P3) | $AA^{x2}$ (P2) | $AA^{x1}$ (P1) | $AA^{y1}$ (P1') | $AA^{y2*}$ (P2') | SEQ ID NO: (if required) |
|---|---|---|---|---|---|---|
| — | — | Leu | Lys | Leu | — | |
| — | — | Leu | Lys | Leu | Leu | SEQ ID NO: 4 |

*If absent, then Y comprises one amino acid, $AA^{y1}$.

Linker Groups

A linker group between the oligopeptide and the therapeutic agent, although optional, may be advantageous for numerous reasons, such as the following:
(1) As a spacer for steric considerations in order to facilitate enzymatic release of the $AA^{y1}$ or $AA^{y2}$ amino acid;
(2) To provide an appropriate attachment chemistry between the therapeutic agent and the oligopeptide;
(3) To improve the synthetic process of making the prodrug conjugate (e.g., by pre-derivatizing the therapeutic agent or oligopeptide with the linker group before conjugation to enhance yield or specificity);
(4) To improve physical properties of the prodrug; and/or
(5) To provide an additional mechanism for intracellular release of the drug.

Linker structures are dictated by the required functionality. Examples of potential linker chemistries are hydrazide, ester, ether, and sulphydryl. Amino caproic acid is an example of a bifunctional linker group. When amino caproic acid is used in the linker group, it is not counted as an amino acid in the numbering scheme of the oligopeptide. Accordingly, examples of suitable linker groups include amino caproic acid, a hydrazide group, an ester group, an ether group and a sulphydryl group.

Therapeutic Agents

Therapeutic agents that are particularly advantageous to modify to a prodrug form according to the invention are those with a narrow therapeutic window. A therapeutic agent with a narrow therapeutic window is one in which the dose at which toxicity is evident, by general medical standards, is very close to the dose at which efficacy is evident.

The therapeutic agent conjugated to the stabilizing group and oligopeptide and, optionally, the linker group to form the prodrug of the invention may be useful for treatment of cancer, inflammatory disease, or some other medical condition. A series of agents can be considered for use in the invention. In fact, they are the same as those that can be used in the prodrug described in Trouet, et al., U.S. Pat. No. 5,962,216 (βAla-Leu-Ala-Leu-DOX). The main structural requirements concerning these agents is the presence of a reactive amino group or the possibility to introduce such a group without critically decreasing the activity.

In addition to therapeutics agents, the invention can also be used with agents that act as chemosensitizers and dyes. The following exemplify such agents and are intended to be merely illustrative and not limiting in any manner. Preferably, the agent is selected from the following classes of compounds: alkylating agents, anthracyclines, antiproliferative agents, camptothecins, chemotherapeutic agents, cyclosporins, dolastatins, enediynes, epipodophyllotoxins, maytansinoids, naphtalimides, platinum coordination complex, pteridines, rhodamines, sulfoximines, taxanes, taxoids, topoiosomerase inhibitors, tubulin binding agents and vinca alkaloids.

Particularly, the agent is advantageously selected from the following compounds, or a derivative or analog thereof: actinomycin D; alkylating agents such as melphalan; amiodarone; anthracyclines such as daunorubicin and doxorubicin; arabinosides such as cytosine arabinoside and adenosine arabinoside, including 1-β-D-arabinofuranosylcytosine; AT-125 or activin (αS, 5S)-α-amino-3-chloro-4,5-dihydro-5-isoxazole acetic acid); bamipine; bleomycin; 5-bromodeoxyuridine; calicheamicin; camptothecins such as 7-amino-methylcamptothecin; L-canavanine; carboplatin; CC-1065; chlorphenoxamine; chloroquine; colchicine; combretastatin and combretastatin $A_4$ phosphate; coumarins such as 7-amino-4-trifluoromethylcoumarin and 7-amino-4-methylcoumarin; cyclophosphamide; cyclosporins such as cyclosporin A; cytarabine; dehydrodidemnin B; dipyridamole; discodermolide; docetaxel; dolastatin 10, dolastatin 11 and dolastatin 15; duocarmycin; epothilone A; etoposide and etoposide phosphate; fludarabine; 5-fluorouracil; folic acid derivatives such as aminopterin, methotrexate and dichloromethotrexate; KW-2189; 6-maytansinoids such as maytansine; mercaptopurine; methopterin; mitomycin C; naphtalimides such as amonafide; nicardipine; nitrosoureas such as N-(2-chloroethyl)-N-nitrosourea; paclitaxel; phenylenediamine mustards such as N,N-bis(2-chloroethyl)-p-phenylenediamine; cis-platin; podophyllotoxin and podophyllotoxin derivatives; porfiromycin; quinidine; quinine; reserpine; rhodamines such as rhodamine 123; sulfoximines such as buthionine sulfoximine, methionine sulfoximine and prothionine sulfoximine; tamoxifen; taxoids such as taxotere; topotecan; trifluoperazine; verapamil; vinca alkaloids such as vinblastine and vincristine; as well as derivatives and analogs thereof.

Some preferred prodrugs contemplated by the invention include the following, shown in Table 4. Those having a "D-Ala" stabilizing group are particularly suitable for intraperitoneal administration, while those having a "Succ-D-Ala" stabilizing group are particularly suitable for intravenous administration:

TABLE 4

| Stabilizing Group | $AA^{x4}$ (P4) | $AA^{x3}$ (P3) | $AA^{x2}$ (P2) | $AA^{x1}$ (P1) | $AA^{y2}$ (P1') | $AA^{y1*}$ (P2') | Drug | SEQ ID NO: (if required) |
|---|---|---|---|---|---|---|---|---|
| D-Ala | — | — | Leu | Lys | Leu | — | DNR | SEQ ID NO: 5 |
| D-Ala | — | — | Leu | Lys | Leu | — | DOX | SEQ ID NO: 5 |
| D-Ala | — | — | Leu | Lys | Leu | Leu | DNR | SEQ ID NO: 6 |
| D-Ala | — | — | Leu | Lys | Leu | Leu | DOX | SEQ ID NO: 6 |
| Succ-D-Ala | — | — | Leu | Lys | Leu | — | DNR | SEQ ID NO: 7 |
| Succ-D-Ala | — | — | Leu | Lys | Leu | — | DOX | SEQ ID NO: 7 |
| Succ-D-Ala | — | — | Leu | Lys | Leu | Leu | DNR | SEQ ID NO: 8 |
| Succ-D-Ala | — | — | Leu | Lys | Leu | Leu | DOX | SEQ ID NO: 8 |

*If absent, then Y comprises one amino acid, $AA^{y2}$.

Multidrug Resistance

Besides toxicity, drug resistance, a state of decreased sensitivity of cancer cells to therapeutic agents that would ordinarily induce cell death, is another major cause of failure in cancer chemotherapy. Resistance can be intrinsic (no response to initial chemotherapy) or acquired (selection of resistant cells in a population of cancer cells in the course of treatment). Such acquired drug resistance is considered the most common reason for the failure of drug treatment in cancer patients with initially sensitive tumors.

The most critical issue is when multidrug resistance ("MDR") occurs. In this case, a given cancer cell appears resistant to a series of different anticancer agents, sometimes with quite different structures and/or mechanisms of action. In this case, overcoming the resistance through combination chemotherapy is far more complicated, and research has focused on discovering agents that are likely to inhibit MDR.

Different mechanisms may be responsible for MDR. The most studied and perhaps the most important one involves the amplification and subsequent overexpression of a gene (mdr1) encoding a transmembrane ATP-dependent protein that pumps the drugs out of the cell lowering the effective concentration at the target site. This pump is a 170,000 Da glycoprotein called gp170 or P-glycoprotein. Particularly high levels of this protein are expressed in normal kidney, liver, pancreas, small intestine, colon and adrenal gland where it might play a role in elimination or secretion mechanisms. As the P-glycoprotein transports therapeutic agents of different chemical structure (vinca alkaloids, anthracyclines, epipodophyllotoxins, actinomycin D, etc), it has been proposed to use non-toxic compounds together with the drugs, that would act as competitors for capture by the pump. Several therapeutic agents have been tried such as verapamil, quinine or trifluoperazine, but toxicity and safety continue to remain an issue.

Accordingly, one aspect of the invention pertains to the use of the oligopeptide described herein, having a stabilizing group at its N-terminus (or C-terminus) and verapamil, quinine, trifluoperazine or another suitable P-glycoprotein inhibitor at its C-terminus (or N-terminus) (optionally separated by a linker group), to act as a P-glycoprotein chemosensitizer, i.e., a competitor for capture by the P-glycoprotein pump.

Another important mechanism of MDR affecting anticancer agents such as nitrogen mustard, melphalan, mitomycin, platinum derivatives, etc. involves increased intracellular reducing capacity as reflected by glutathione ("GSH") levels. GSH normally protects cells by reacting with electrophile derivatives and reactive oxygen species, and in cancer cells, acquired resistance to alkylating agents has been associated with increased GSH. These observations led to the development of inhibitors of γ-glutamylcysteine synthetase (the enzyme involved in GSH biosynthesis) as potential modulators of this type of resistance. Several interesting results have been obtained with one such compound, buthionine sulfoximine. However, due to the important physiological role of GSH, this type of compound is not devoid of toxicity.

Whether considering the implications of P-glycoprotein-mediated or GSH-mediated MDR, it may be preferable to increase the specificity of action of the existing therapeutic agents, rather than to look for other potential modulators. The oligopeptides described herein can be used to obtain prodrugs of multidrug resistance modifiers.

It is particularly important to notice that such modulators of MDR are generally used not as single agents but as part of a chemotherapeutic regimen. Two types of use of the prodrugs of these MDR modulators are contemplated by the invention: (i) use of these prodrugs together with classical treatments, and (ii) use of these prodrugs with treatments based on the less toxic prodrugs of the classically used anticancer agents described herein. The latter type of use could even lead to better results on resistant cells, since the prodrugs of the anticancer agents are supposed to lead to higher intracellular drug concentrations.

Accordingly, another aspect of the invention pertains to the use of the oligopeptide described herein, having a stabilizing group at its N-terminus (or C-terminus) and buthionine sulfoximine or another suitable γ-glutamylcysteine synthetase inhibitor at its C-terminus (or N-terminus) (optionally separated by a linker group), to inhibit GSH production.

Both the (stabilizing group)-(oligopeptide)-(optional linker group)-(P-glycoprotein inhibitor) and the (stabilizing group)-(oligopeptide)-(optional linker group)-(γ-glutamylcysteine synthetase inhibitor) described above would find utility in methods of treating a patient.

Screening of the Prodrug

The synthesized prodrug can be tested against a test standard such as the plasmin substrate, D-Ala-Leu-Lys, conjugated to a marker, 7-amido-4-methylcoumarin. The rates of hydrolysis of the synthesized peptidyl prodrug and the test standard by plasmin are compared under common experimental conditions. The General Methods, Section N., below, provides an exemplary scheme for performing this test.

The disclosure of making and using the prodrugs taught herein provides a useful alternative to prior teachings of prodrug design. As illustrated in the examples below, the prodrugs of the invention are efficacious and well-tolerated in vivo in animal models. As such, the prodrugs are advantageously utilized in therapy.

Prodrug Design

A method of designing a prodrug is another aspect of the invention and entails initially selecting a peptide of two-five amino acids, then adding one or two amino acids having large aliphatic side chains (e.g., Leu) to form an oligopeptide. The oligopeptide is linked at a first attachment site of the oligopeptide to a stabilizing group that hinders cleavage of the oligopeptide by enzymes present in whole blood, and directly or indirectly linked to a therapeutic agent at a second attachment site of the oligopeptide. The linkage of the oligopeptide to the therapeutic agent and the stabilizing group may be performed in any order or concurrently. The resulting conjugate is tested for cleavability by plasmin under given experimental conditions. The standard rate of cleavage is tested on a test standard by plasmin under the same given experimental conditions. The test standard consists of a conjugate of D-Ala-Leu-Lys and the marker, 7-amido-4-methylcoumarin. The first attachment site is usually the N-terminus of the oligopeptide but may be the C-terminus of the oligopeptide or another part of the oligopeptide. The second attachment site is usually the C-terminus of the oligopeptide, but may be the N-terminus of the oligopeptide or another part of the oligopeptide. A prodrug designed by such a method is also part of the invention.

Further, the invention includes a method for decreasing toxicity of a therapeutic agent that is intended for administration to a patient. Specifically, a modified, prodrug form of the therapeutic agent is formed by directly or indirectly linking the therapeutic agent to an oligopeptide that is cleavable by plasmin under physiological conditions. The prodrug provides for decreased toxicity of the therapeutic agent when administered to the patient. The modification of the therapeutic agent in this manner also allows for administration of an increased dosage of the therapeutic agent to the patient relative to the dosage of the therapeutic agent in unconjugated form.

Pharmaceutical Compositions

The invention also includes a pharmaceutical composition comprising a compound, particularly a prodrug compound, according to the invention and, optionally, a pharmaceutically acceptable adjuvant or vehicle.

The invention also relates to the use of the pharmaceutical composition for the preparation of a medicinal product intended for the treatment of a medical condition.

The pharmaceutical composition may, for example, be administered to the patient parenterally, especially intravenously, intramuscularly, or intraperitoneally. Pharmaceutical compositions of the invention for parenteral administration comprise sterile, aqueous or nonaqueous solutions, suspensions, or emulsions. As a pharmaceutically acceptable solvent or vehicle, propylene glycol, polyethylene glycol, injectable organic esters, for example ethyl oleate, or cyclodextrins may be employed. Isotonic saline may be part of the pharmaceutical composition. These compositions can also comprise wetting, emulsifying and/or dispersing agents.

The sterilization may be carried out in several ways, for example using a bacteriological filter, by incorporating sterilizing agents in the composition or by irradiation. They may also be prepared in the form of sterile solid compositions, which may be dissolved at the time of use in sterile water or any other sterile injectable medium.

The pharmaceutical composition may also comprise adjuvants that are well known in the art (e.g., vitamin C, antioxidant agents, etc.) and capable of being used in combination with the compound of the invention in order to improve and prolong the treatment of the medical condition for which they are administered.

Doses for administration to a patient of the compounds according to the invention are generally at least the usual doses of the therapeutic agents known in the field, described in Chabner, et al., Cancer Chemotherapy (Lippincott ed., ISBN 0-397-50900-6, 1990) or they may be adjusted, within the judgment of the treating physician, to accommodate the superior effectiveness of the prodrug formulations or the particular circumstances of the patient being treated. Hence, the doses administered vary in accordance with the therapeutic agent used for the preparation of the compound according to the invention.

Treatment of Patients with Prodrug Compound

A method for the therapeutic treatment of a medical condition that involves administering, preferably parenterally and more preferably intravenously, to the patient a therapeutically effective dose of the pharmaceutical composition is also within the scope of the invention. Thus, the method generally entails administering to the patient a therapeutically effective amount of a compound comprising:

(1) a therapeutic agent capable of entering a target cell;

(2) an oligopeptide having the formula X-Y, where X is a plasmin peptide substrate of 2-4 amino acids and Y is a peptide comprising 1-2 aliphatic amino acids having large lateral chains;

(3) a stabilizing group; and (4) optionally, a linker group not cleavable by plasmin;

wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide;

wherein the stabilizing group hinders cleavage of the oligopeptide by enzymes present in whole blood; and wherein the compound is cleaved by plasmin.

The oligopeptide can also be described as having the formula or sequence: $(AA^x)_m$-$(AA^y)_n$ (SEQ ID NO:1) wherein: $(AA^x)_m$ is a plasmin substrate and each $AA^x$ independently represents an amino acid; each $AA^y$ independently represents an aliphatic amino acid having a large lateral chain; m is an integer from 2-4; and n is an integer from 1-2.

The prodrug compound is useful for the treatment of many medical conditions including cancer, neoplastic diseases, tumors, inflammatory diseases, and infectious diseases. Examples of preferred diseases are breast cancer, colorectal cancer, liver cancer, lung cancer, prostate cancer, ovarian cancer, brain cancer, and pancreatic cancer. Formulated in pharmaceutically acceptable vehicles (such as isotonic saline), the prodrug compound can be administered to animals or humans in intravenous doses ranging from 0.05 mg/kg/dose/day to 300 mg/kg/dose/day. It can also be administered via intravenous drip or other slow infusion method.

Human patients are the usual recipients of the prodrug of the invention, although veterinary usage is also contemplated.

Diagnosis or Assay

An article of manufacture, such as a kit, for diagnosis or conducting an assay is also within the scope of the invention. Such an article of manufacture would preferably utilize a compound as described above, except that a marker, such as coumarin, is conjugated to the oligopeptide and stabilizing group instead of a therapeutic agent. At least one reagent useful in the detection of the marker is typically included as part of the kit. Thus, the article of manufacture would include the following:

(1) a compound comprising:

(a) a marker;

(b) an oligopeptide having the formula X-Y, where X is a plasmin peptide substrate of 2-4 amino acids and Y is a peptide comprising 1-2 aliphatic amino acids having large lateral chains;

(c) a stabilizing group; and (d) optionally, a linker group not cleavable by plasmin;

wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide;

wherein the stabilizing group hinders cleavage of the oligopeptide by enzymes present in whole blood; and wherein the compound is cleavable by plasmin; and (2) at least one reagent useful in the detection of the marker.

As noted above, the standard rate of cleavage is tested on a test standard by plasmin under the same experimental conditions and the test standard consists of a conjugate of a plasmin substrate and a marker, for example D-Ala-Leu-Lys-7-amido-4-methylcoumarin. Further, the oligopeptide can also be described as having the formula or sequence $(AA^x)_m$-$(AA^y)_n$.

The article of manufacture may be used, for example, with patient samples to diagnose tumors or to identify patients susceptible to treatment by prodrug therapy.

Process Chemistry General Procedures

Oligopeptide: General Method for the Synthesis of Peptides

The peptide or oligopeptide sequences in the prodrug conjugates of this invention may be synthesized by the solid phase peptide synthesis (using either Boc or Fmoc chemistry) methods or by solution phase synthesis. The general Boc and Fmoc methods are widely used and are described in the following references: Merrifield, J. A. *Chem. Soc.*, 88:2149, 1963; Bodanszky and Bodanszky, *The Practice of Peptide Synthesis*, Springer-Verlag, Berlin, 7-161, 1994; Stewart, *Solid Phase Peptide Synthesis*, Pierce Chemical, Rockford, 1984.

General Fmoc Solid Phase Method

Using the preferred solid phase synthesis method, either automated or manual, a peptide of desired length and sequence is synthesized through the stepwise addition of amino acids to a growing chain which is linked to a solid resin. Examples of useful Fmoc compatible resins include, but are not limited to, Wang Resins (Wang, *J. Am. Chem. Soc.* 95:1328, 1973 and Zhang, et al., *Tet. Lett.* 37:5457, 1996), HMPA-PEGA resin, Rink Resins (Rink, *Tet. Lett.* 28:3787, 1987), or a hydroxyethyl-photolinker resin. The C-terminus of the peptide chain is covalently linked to a polymeric resin and protected α-amino acids were added in a stepwise manner with a coupling reagent. A preferred α-amino protecting group is the Fmoc group, which is stable to coupling conditions and can readily be removed under mild alkaline conditions. The reaction solvents are preferably but not limited to DMF, NMP, DCM, MeOH and EtOH. Examples of coupling agents are: DCC, DIC, HATU and HBTU. Cleavage of the N-terminal protecting group is accomplished in 10-100% piperidine in DMF at 0-40° C., with ambient temperature being preferred. At the end of synthesis, the final Fmoc protecting group is removed using the above N-terminal cleavage procedure. The remaining peptide on resin is cleaved from the resin along with any acid sensitive side chain protecting groups by treating the resin under acidic conditions. For example, an acidic cleavage condition is a mixture of TFA in DCM. If the hydroxyethyl-photolinker resin is used, the appropriate wavelength for inducing cleavage is λ365 nm ultraviolet light.

General N-Cap Method Via Solid Phase Synthesis

The preparation of N-terminus derivatized peptides is conveniently accomplished on a solid phase. When the peptide synthesis is complete, the terminal Fmoc is removed while the peptide is still on the solid support. The N-cap of choice is coupled next using standard peptide coupling conditions onto the N-terminus of the peptide. On completion of the N-cap coupling the peptide is cleaved from the resin using the procedure described above.

General Boc Solid Phase Method

For the solid phase method using Boc chemistry, either the Merrifield resin or PAM resin is useful. The amino acids are coupled to the growing chain on solid phase by successive additions of coupling agent activated Boc-protected amino acids. Examples of coupling agents are: DCC, DIC, HATU and HBTU. The reaction solvents may be DMF, DCM, MeOH and NMP. Cleavage of the Boc protecting group is accomplished in 10-100% TFA in DCM at 0-40° C., with ambient temperature being preferred. On completion of the peptide chain assembly the N-terminus protecting group (usually Boc) is removed as described above. The peptide is removed from the resin using liquid BF or trifluoromethane sulfonic acid in DCM. Schemes I and II illustrate the Merrifield solid phase peptide synthesis ("SPPS") method.

SCHEME I

Step A: Boc-deprotection step

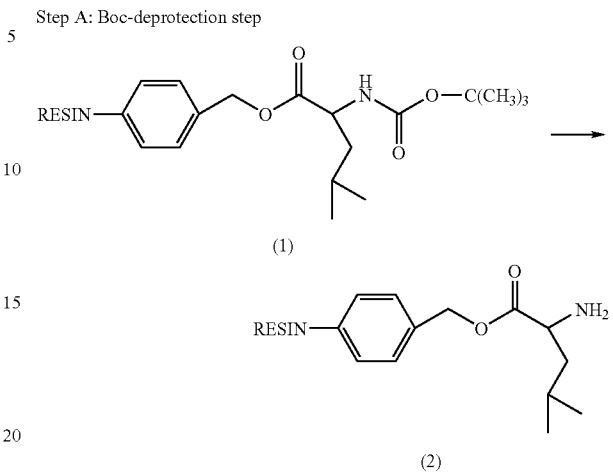

N-α-Protecting Boc of the amino acid directly attached to the Boc-Leu-Merrifield Resin (1) is first cleaved in the vessel for manual SPPS by vigorous shaking with a mixture of TFA:CH$_2$Cl$_2$ (1:1, v/v) for 30 min at RT to yield NH$_2$-Leu-Merrified Resin (2). This procedure, called Boc-deprotection can be performed as follows (solvent volumes given for 10 g of resin).

| | | |
|---|---|---|
| CH$_2$Cl$_2$ | 60 ml | 3 × 1 min |
| TFA:CH$_2$Cl$_2$ (1:1) | 50 ml | 1 × 1 min |
| TFA:CH$_2$Cl$_2$ (1:1) | 50 ml | 1 × 30 min |
| CH$_2$Cl$_2$ | 50 ml | 6 × 1 min |
| DIPEA 5% (v/v) in CH$_2$Cl$_2$ | 50 ml | 3 × 2 min |
| CH$_2$Cl$_2$ | 50 ml | 6 × 1 min |

Step B: N-Protected Amino Acid Attachment

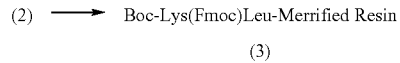

3 eq. of the Boc-protected amino acid to attach next, for example, Boc-Lys(Fmoc)-OH, is dissolved in CH$_2$Cl$_2$ (45 ml) and put into contact with the resin (2) under shaking for 10 min. 3 eq. of DCC is dissolved in CH$_2$Cl$_2$ (5 ml) and added into the reaction mixture. The latter is agitated for 2 hours at RT to produce Boc-Lys(Fmoc)-Leu-Merited Resin (3). The reaction is then checked by the ninhydrin test for completeness.

The ninhydrin test uses three solutions: Solution A contains 50 mg ninhydrin in 10 ml EtOH; Solution B contains 80 mg phenol in 20 ml EtOH; and Solution C contains 2 ml KSCN 0.01M in H$_2$O in 100 ml pyridine. A few milligrams of the product to be tested is introduced in a test tube, and two drops of Solution A, two drops of Solution B, and two drops of Solution C are added. The mixture is heated in a boiling water bath for five min and 1 ml of EtOH is added. If the reaction is complete, the liquid remains colorless. Blue coloration of the material indicates the presence of a free amino groups with an intensity proportional to their concentration.

If the ninhydrin test is negative (i.e., colorless), the Boc-attachment step is considered to be complete. If positive (i.e., blue), a new coupling procedure step with the same quantity of reagents is repeated.

Step C: Attachment of Amino Acids

Attachment of subsequent amino acids involves repeating Steps A and B, as needed:

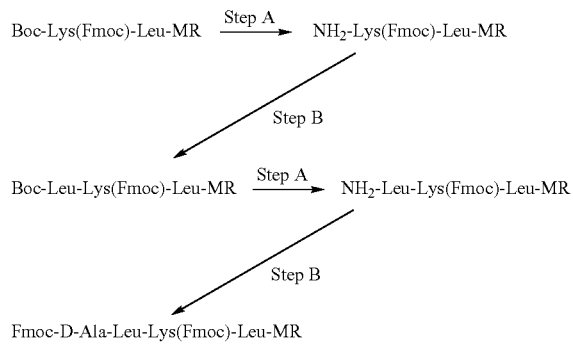

where "MR" is the Merrifield Resin.

The final coupling step with this technique generally includes a Fmoc-protected amino acid, designed to terminate the sequence the be synthesized (the same proportions of reagents and procedures being employed as in the case of Boc-protected amino acids).

Step D: Cleavage of the Fmoc-Protected Tetrapeptide (Fmoc-D-Ala-Leu-Lys(Fmoc)-Leu-OH) from the Resin The Fmoc-protected peptide is removed from the resin by the addition of HBr (30% in MeOH):TFA (1:1) for 30 min. This is followed by treatment with TFA (3×) and $CH_2Cl_2$ (6×).

Alternately, the Fmoc-protected peptide removal from the resin can be achieved by incubating the product in the following solutions:

| | | | |
|---|---|---|---|
| $CH_2Cl_2$ | 50 ml | 1 × 10 min | discard |
| TFA:$CH_2Cl_2$ (1:1, v/v) | 50 ml | 1 × 10 min | discard |
| TFA | 50 ml | 1 × 30 min | discard |
| TFA | 50 ml | 1 × 30 min | discard |
| TFA:HBr (1:1, v/v) | 60 ml | 1 × 30 min | recover |
| TFA | 50 ml | 3 × 3 min | recover |
| $CH_2Cl_2$ | 50 ml | → colorless | recover |

Step E: Solvent Evaporation, Dissolution in MeOH and Precipitation in $H_2O$

The solvent is repeatedly evaporated (the solid redissolved in $CH_2Cl_2$) until the disappearance of an acid odor (at least 5 times). The product is dissolved in MeOH. A large quantity of ice-cold water (at least 95% of the resulting volume, w/v) is then added, the mixture stirred and the precipitate filtered on frit glass. The Fmoc-protected peptide is then lyophilized.

The following scheme provides the synthesis route for Compounds I and II, using DNR HCl or DNR-Leu HCl, respectively, as the starting materials. It is understood, however, that other anthracycline prodrugs and prodrugs of other therapeutic agents can be synthesized in a similar manner, or by techniques that are well known to those of skill in the art.

SCHEME II

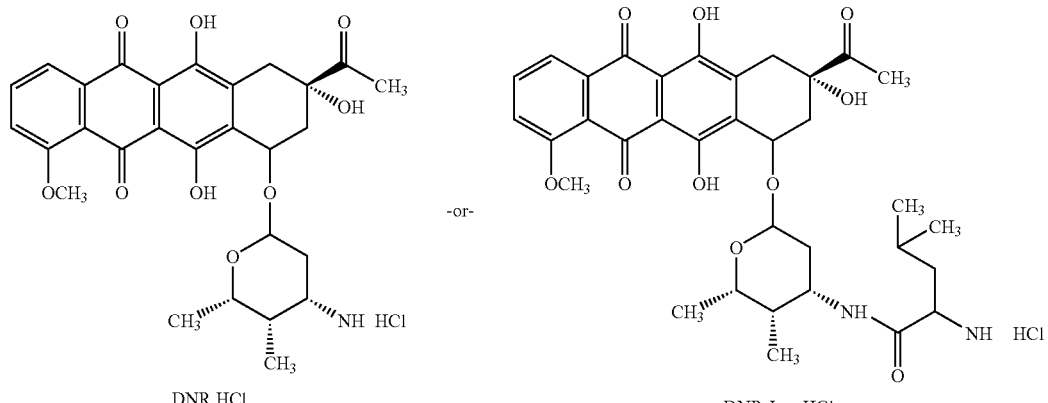

COUPLING
1) DMF, 45 ml/mmole
2) Fmoc-D-Ala-L-Leu-L-Lys(Fmoc)-L-Leu-OH, 1 eq.
3) DIPEA, 2 eq.
4) 15 min stirring at RT
5) HATU, 1.1 eq. in DMF (10 ml/mmole)
6) 2 hours stirring at RT
7) 2 volumes $H_2O$, 4° C., stirring
8) Filtration of the precipitate
9) 6 × lactate buffer, 1% solution, 4° C. (optional)
10) Air drying of the precipitate Fmoc-D-Ala-L-Leu-L-Lys(Fmoc)-L-Leu-anthracycline -or- Fmoc-D-Ala-L-Leu-L-Lys(Fmoc)-L-Leu-L-Leu-anthracycline DEPROTECTION
1) DMF (50 ml/mmole), piperidine 100 eq., RT, 5 min
2) Bath -20° C., 2 vol lactate buffer 10% (v/v), pH 3.0, 4° C.
3) CH$_2$Cl$_2$ liquid-liquid extraction
4) CG-71sd Amberchrome solid phase extraction
5) Evaporation of solvents, dissolution in H$_2$O, lyophilisation

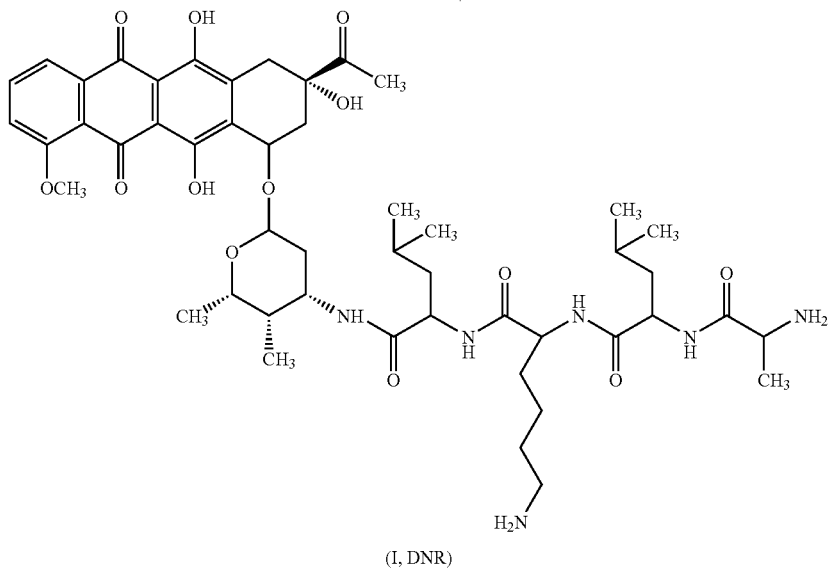

(I, DNR)

-or-

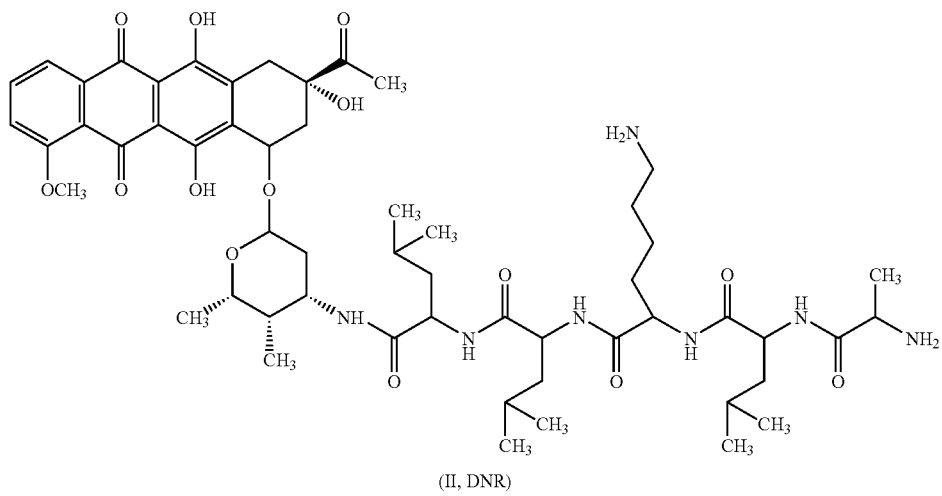

(II, DNR)

General Procedure for the Preparation of Fmoc Oligopeptide by Solution Phase Synthesis Alternatively, the prodrug peptide intermediate may be made via a solution phase synthesis, utilizing either Boc or Fmoc chemistry. The peptide can be built up by the stepwise assembly in analogy to the solid phase method (in the N-terminal direction or in the C-terminal direction) or through the coupling of a dipeptide with a single amino acid.

One method of solution phase synthesis is a stepwise building up of the prodrug peptide intermediate using Fmoc chemistry. The C-terminus must first be protected to reduce the formation of side products. The C-terminal group in is typically Me, tBu, Bz or TCE. (Note when the N-cap is methyl succinyl the C-terminus group cannot be methyl.). DMF is a common solvent, as are DMSO, CH$_3$CN and NMP (or mixtures thereof). Pyridine, TEA or other bases may be substituted for piperidine in deprotecting the growing peptide chain protected amino terminus. HBTU is a common activating agent, but other activating agents such as DCC, DIC, DCC+ HOBT, OSu, activated esters, azide, or triphenyl phosphoryl azide can also be used. Additionally, the protected peptide acid chloride or acid bromide may be used to couple directly to the amino acid or peptide fragment. On completion of the oligopeptide assembly, the N-terminus is deprotected and the C-terminus protected peptide is ready to accept the desired N-cap.

General Procedure for the Preparation of N-Cap Oligopeptide Via Solution Phase Synthesis When constructing the N-capped oligopeptide by solution phase synthesis, the N-cap needs to be synthesized by a slightly modified procedure. First the C-terminus of the Fmoc oligopeptide needs to be protected with an acid labile or hydrogenation sensitive protecting group compatible with the selective deprotection of the C-terminus over the N-cap. Then the Fmoc protecting group needs to be removed from the oligopeptide to reveal the N-terminus. With the N-terminus deprotected and the C-terminus protected, the oligopeptide is reacted with the activated hemiester of the desired N-cap. The N-cap can be activated using methods for activating amino acids such as DCC or HATU in base and an appropriate solvent. Alternatively, where MeOSucc is used, the coupling may also be done via methyl hemisuccinyl chloride (or other acid halide) using an inert solvent in the presence of an organic or inorganic base, such as DIPEA, TEA or $Cs_2CO_3$. One example of such a synthesis can be by reacting MeOSucc and (Amino acid)$_i$-benzyl ester. The coupling method can be any one of the methods generally used in the art (see for example: Bodanszky, *The Practice of Peptide Synthesis*, Springer Verlag, 185, 1984; and Bodanszky, *Principles of Peptide Synthesis*, Springer Verlag, 159, 1984. The benzyl group then can be removed by catalytic hydrogenation providing the desired N-cap methylsuccinyl form of the oligopeptide. Other examples of suitable, selectively removable C-terminal protecting groups can be, but are not limited to, tBu, alkoxy-methyl and TCE. Other methods of accomplishing this step are described in the literature.

The reaction conditions are well known in the art and detailed in the citations given. The advantage of the above described methods is the facile purification of the product produced by solution phase synthesis.

Prodrug Conjugate

General Methods for the Conjugation and Deprotection Steps

The prodrugs described herein can be synthesized by coupling an Fmoc form (which means Fmoc is attached to the N-terminus of the oligopeptide) of the oligopeptide with daunorubicin, or doxorubicin, or any appropriate therapeutic agent using any of the standard activating reagents used in peptide synthesis. The solvent may be toluene, ethyl acetate, DMF, DMSO, $CH_3CN$, NMP, THF, DCM or any other suitable inert solvent as is known in the art and the reagents are soluble therein. Preferred solvents include DMF and NMP. The appropriate temperature range is −25 to +25° C., with ambient temperature being preferred. The activating agent may be selected from one of the following: PyBOP, HBTU, HATU, DIC, DCC, DCC+HOBT, OSu activated esters, azide, or triphenylphosphorylazide. HBTU or HATU are preferred activating agents. Alternatively, the acid chloride or the acid bromide of the protected peptide can also be used for this coupling reaction. 2-4 equivalents, advantageously 2-2.5 equivalents of a base is required for the coupling reaction. The base can be selected from inorganic bases such as $CsCO_3$, Na— or $K_2CO_3$, or organic bases, such as TEA, DIPEA, DBU, DBN, DBO, pyridine, substituted pyridines, N-methylmorpholine etc., preferably TEA, or DIPEA. The reaction can be carried out at temperatures between −15° C. and 50° C., advantageously between −10° C. and 10° C. The reaction time is between 5-90 minutes and is advantageously 20-40 minutes. The product is isolated by pouring the reaction mixture into water and filtering the precipitate formed. The crude product can be further purified by recrystallization from DCM, THF, ethyl acetate, or ACN, preferably from DCM or ACN. The isolated Fmoc form of the (oligopeptide)-(therapeutic agent) conjugate is then deprotected over 2-90 minutes, preferably 3-8 minutes, using a ten- to hundred-fold excess of base at a temperature between −10° C. and 50° C. Ideally, 5-60 equivalents of the base are preferred. Piperidine is the preferred base to deprotect Fmoc groups. The deprotected amino terminus of the (oligopeptide)-(therapeutic agent) conjugate is acylated by a diacid anhydride as an activated hemiester to give the final N-cap form of the oligopeptide-therapeutic agent.

Alternatively, the final prodrug can be similarly prepared from the protected N-cap form of the oligopeptide such as a methylhemiester form of succinyl-N-cap oligopeptide and conjugated to a therapeutic agent.

The (protected N-Cap)-(oligopeptide)-(therapeutic agent) conjugate is now deprotected by methods compatible to the stability of the therapeutic agent. For other therapeutic agents, benzyl protecting groups and catalytic hydrogenation to deprotect might be chosen.

Conversion to the salt form of the negatively charged (N-cap)-(oligopeptide)-(therapeutic agent) is carried out with a solvent selected from the following group: alcohol (including MeOH, EtOH or isopropanol), water, ACN, THF, diglyme or other polar solvents. The sodium source is one molar equivalent of $NaHCO_3$, NaOH, $Na_2CO_3$, NaOAc, $NaOCH_3$ (in general sodium alkoxide), or NaH. An ion exchange column charged with $Na^+$ (such as strong or weak ion exchangers) is also useful for this last step of making the salt form of the (N-cap)-(oligopeptide)-(therapeutic agent) when appropriate. Sodium is described in this application as an example only.

Generally, the prodrug may be converted to a pharmaceutically acceptable salt form to improve solubility of the prodrug. The (N-cap)-(oligopeptide)-(therapeutic agent) is neutralized with a pharmaceutically acceptable salt, e.g., $NaHCO_3$, $Na_2CO_3$, NaOH tris(hydroxymethyl)-aminomethane, $KHCO_3$, $K_2CO_3$, $CaCO_3$, $NH_4OH$, $CH_3NH_2$, $(CH_3)_2NH$, $(CH_3)_3N$, acetyltriethylammonium. The preferred salt form of prodrug is sodium and the preferred neutralizing salt is $NaHCO_3$.

It is well documented that anthracycline type molecules, including doxorubicin and daunorubicin form gels in organic solvents in very low concentrations (Matzanke, et al., *Eur. J. Biochem.* 207:747-55, 1992; Chaires, et al., *Biochemistry* 21:3927-32, 1982, and Hayakawa, et al., *Chem. Pharm. Bull.* 39:1282-6, 1991). This may be a considerable obstacle to getting high yields of clean product when making peptide anthracycline conjugates. The gel formation contributes to the formation of undesirable side reactions. One way to minimize this problem is to use very dilute solutions (1-2%) for the coupling reaction, however it is not practical in a process environment (large amounts of waste, complicated isolation). To overcome this problem, urea or other chaotropic agents may be used to break up the strong hydrophobic and hydrogen bonding forces forming the gel. Thus if the coupling reaction is carried out in a urea-containing solvent, advantageously a 20% to saturated solution of urea in DMF or NMP, the side reactions can be kept below 2% even if the concentration of reactants exceeds 10%. This procedure makes the conjugation step practical at high concentrations and produces good yields and improved purity over the procedures that do not use urea or other chaotropic agents.

General Enzyme Method

Hydrolysis of protected N-cap-oligopeptide therapeutic agents to the full N-cap compound catalyzed by acids or bases leads to complex reaction mixtures due to the lability of many therapeutic agents even under moderately acidic or basic conditions. Enzymes can promote the hydrolysis without destroying the substrate or the product. Enzymes suitable for this reaction can be esterases or lipases and can be in their natural, water soluble forms or immobilized by cross coupling, or attachment to commercially available solid support materials. Of the soluble enzymes evaluated, *Candida Antarctica* "B" lipase (Altus Biologics) is especially useful. example of an enzyme immobilized by cross coupling is ChiroCLEC-PC™ (Altus Biologics). *Candida Antarctica* "B" lipase (Altus Biologics) can be immobilized by reaction with NHS activated Sepharose™ 4 Fast Flow (American Pharmacia Biotech). The pH of the reaction mixture during the hydrolysis is carefully controlled and maintained by a pH-stat between 5.5 and 7.5, advantageously between 5.7 and 6.5, via controlled addition of $NaHCO_3$ solution. When the reaction is completed the product is isolated by lyophilization of the filtered reaction mixture. The immobilized enzymes remain on the filter cake and can be reused if desired.

General Allyl or Alkyl Ester Method

The prodrug can also be prepared via coupling an allyl-hemiester or alkyl-hemiester form of the N-cap oligopeptide with a therapeutic agent and then liberating the free acid from the conjugate. The coupling of allyl-succinyl-(Amino acid)$_i$- with doxorubicin can be carried out via any one of the oligopeptide conjugation methods.

Allyl-succinyl-(Amino acid)$_i$-doxorubicin can also be synthesized by reacting allyl hemisuccinate, which is prepared via known methods (Casimir, et al., *Tet. Lett.* 36:19, 3409, 1995), with (Amino acid)$_i$-doxorubicin similarly as coupling of the protected peptidyl precursors to doxorubicin was described in the previous methods. Suitable inert solvents are THF, DCM, ethyl acetate, toluene, preferably THF from which the acid form of the product precipitates as the reaction progresses. The isolated acid is converted to its sodium salt as described earlier. Reaction times vary between 10-180 minutes, advantageously 10-60 minutes, at temperatures between 0-60° C., preferably 15-30° C.

Removal of the allyl or alkyl group can be done with Pd(0), or Ni(0), advantageously Pd(0) promoted transfer of the allyl or alkyl group to acceptor molecules, as it is well known in the art and documented in the professional literature (Genet, et al., *Tet. Lett.* 50:497, 1994; Bricout, et. al., *Tet. Lett.* 54:1073, 1998, Genet, et. al., *Synlett* 680, 1993; Waldmann, et. al., *Bioorg. Med. Chem.* 7:749, 1998; Shaphiro, et al., *Tet. Lett.* 35:5421, 1994). The amount of catalyst can be 0.5-25 mol % to the substrate.

General Trityl or Substituted Trityl Method

The prodrug may also be synthesized by utilizing an R'-oligopeptide, where R' is trityl or substituted trityl. The coupling of R'-oligopeptide with a therapeutic agent can be carried out via any one of the methods described earlier for conjugation of a protected oligopeptide with a therapeutic agent at 30-120 minutes at 0-20° C.

Removal of trityl or substituted trityl group can be achieved under acidic conditions to give the positively charged prodrug, which is N-capped as described above. The trityl deprotection can be accomplished with acetic acid, formic acid and dilute hydrochloric acid.

The prodrug can be converted into (succinyl or glutaryl)-(oligopeptide)-(therapeutic agent) conjugate by reacting with succinic anhydride or glutaric anhydride. The solvent for coupling step DMF, DMSO, $CH_3CN$, NMP, or any other suitable solvent is known in the art. Succinyl or glutaryl oligopeptide therapeutic agents can be converted to any pharmaceutically acceptable salt.

General Inverse Direction Solid Phase Conjugation Method

The prodrug compound of the present invention can be synthesized by using solid phase chemistry via "step wise" inverse (from the N-terminal to the C-terminal) direction methods.

One way is to use resins to immobilize a succinyl hemiester, for example succinyl-mono-benzyl ester or -allyl ester. Examples of resins could be selected are Wang Resins; Rink Resins; and Trityl-, or substituted-trityl Resins (Chen, et. al., *J. Am. Chem. Soc.* 116:2661, 1994; Bartos, et. al., Peptides, Proc. 22$^{nd}$ European Peptide Symposium, 1992; and Schneider, et al., (Eds.), ESCOM, Leiden, pp. 281, 1993). The immobilized ester is then deprotected and reacted with, for example, a similarly C-terminal protected methionine. These steps are then repeated with appropriate amino acid residues, followed by the coupling of doxorubicin to the immobilized succinyl-tripeptide. The molecule is then liberated from the resin by using mildly acidic conditions to form a free prodrug, such as free Succ-(Amino acid)$_j$-Leu-DOX. Another version of phase synthesis utilizes immobilized succinyl oligopeptide ester. This is then C-terminally deprotected, followed by the coupling step to doxorubicin or other therapeutic agent, and finally liberated from the resin. The acid form of the prodrug molecule may then be converted finally into its sodium salt as described above.

Removal of Free Therapeutic Agent

Unconjugated therapeutic agent may be present late in the process of making the prodrug. For example, during the coupling step of (stabilizing group)-(oligopeptide) conjugate with doxorubicin as the therapeutic agent, it has been found in some instances, that the reaction does not proceed completely. Initial attempts to remove doxorubicin completely can be attempted by acidic washes. In the event that such attempts do not result in complete removal, any remaining free therapeutic agent can be removed by a process that utilizes scavenging resin or beads.

The crude product, which contains the intermediate and residual doxorubicin, is dissolved in DMF and polystyrene methylisocyanate or polystyrene sulfonyl chloride resin or beads are added. The reaction is then stirred for 60 minutes. The free amino group of doxorubicin reacts with the isocyanate or sulfonyl chloride group on the beads to form a urea or sulfonamide derivative. The solid beads with doxorubicin attached to them are then separated from the desired product by filtration. The desired product remains in the DMF solution. This approach seems to be a very mild and effective method for removing residual therapeutic agent from the product.

Thus, the invention includes a method of making a compound comprising:
(1) selecting an Fmoc-protected oligopeptide having a formula, Fmoc-$(AA^x)_m$-$(AA^y)_n$, where $AA^x$, $AA^y$, m and n are as defined above;
(2) coupling the Fmoc-protected oligopeptide to a therapeutic agent by activating the Fmoc-protected oligopeptide with an activating agent in the presence of the therapeutic agent to form an Fmoc-protected oligopeptide-therapeutic agent conjugate;
(3) deprotecting the Fmoc-protected oligopeptide-therapeutic agent conjugate by contacting it with a base to form an oligopeptide-therapeutic agent conjugate; and
(4) coupling the oligopeptide-therapeutic agent conjugate to a stabilizing group to form the compound.

Alternatively, a method of making a compound comprises the following steps:
(1) selecting an oligopeptide having the formula, $(AA^x)_m$-$(AA^y)_n$, where $AA^x$, $AA^y$, m and n are as defined above;
(2) coupling the oligopeptide to an alkyl ester-protected stabilizing group to form an alkyl ester-protected stabilizing group-oligopeptide conjugate;
(3) coupling the alkyl ester-protected-stabilizing group-oligopeptide conjugate to a therapeutic agent by activating the alkyl ester-protected stabilizing group-oligopeptide conjugate with an activating agent in the presence of a therapeutic agent to form an alkyl ester-protected stabilizing group-oligopeptide-therapeutic agent conjugate; and
(4) deprotecting the alkyl ester-protected stabilizing group-oligopeptide therapeutic agent conjugate to form the compound.

A compound of the invention may also be made via the following steps:
(1) selecting an oligopeptide having the formula, $(AA^x)_m$-$(AA^y)_n$, where $AA^x$, $AA^y$, m and n are as defined above;
(2) coupling the oligopeptide to an allyl ester-protected stabilizing group to form an allyl ester-protected stabilizing group-oligopeptide conjugate;
(3) coupling the allyl ester-protected-stabilizing group-oligopeptide conjugate to a therapeutic agent by activating the allyl ester-protected stabilizing group-oligopeptide conjugate with an activating agent in the presence of a therapeutic agent to form an allyl ester-protected stabilizing group-oligopeptide-therapeutic agent conjugate; and
(4) deprotecting the allyl ester-protected stabilizing group-oligopeptide therapeutic agent conjugate to form the compound.

Yet another method for making a compound of the invention comprises the following steps:
(1) selecting a trityl-protected oligopeptide having a formula, trityl-$(AA^x)_m$-$(AA^y)_n$, where $AA^x$, $AA^y$, m and n are as defined above;
(2) coupling the trityl-protected oligopeptide to a therapeutic agent by activating the trityl-protected oligopeptide with an activating agent in the presence of a therapeutic agent, thereby making a trityl-protected oligopeptide-therapeutic agent conjugate;
(3) deprotecting the trityl-protected oligopeptide-therapeutic agent conjugate under acidic conditions to form an oligopeptide-therapeutic agent conjugate; and
(4) coupling the oligopeptide-therapeutic agent conjugate with an stabilizing group to form the compound.

Another possible step in connection with any of these methods is removing uncoupled therapeutic agent by use of scavenging resin or beads. Further, the compound may be neutralized with a pharmaceutically acceptable salt if desired.

The present invention will be described in greater detail in the examples which follow, given by way of non-limiting illustration of the present invention.

EXAMPLES

General Methods

A. Synthesis of Amino Acid Derivatives of DNR by a Progressive Elongation of the Peptidic Sequence
  1. Products
  DNR-HCl; Fmoc-protected amino acids (Novabiochem); DIPEA (98+%, Acros); DMF (Uvasol for spectroscopy, Merck); HATU (97%, Aldrich); apyrogen water (Baxter); lactate buffer (L-Lactic acid in 85% water, Aldrich and NaOH 1N, Vel); piperidine (>99%, Fluka); chloroform (analytical reagent, Labscan); sodium sulfate (Vel); MeOH (analytical reagent, Labscan); $Et_2O$ (>99.8%, Fluka); N-hexane (99%, Labscan); glutaric anhydride (97%, Acros); C180DS-A silica gel (40-60 µm, 120 Å, YMC).
  2. Synthesis of (Amino Acid)$_{n+1}$-DNR
  Piperidine (50.0 eq.) was added to a solution of Fmoc-(Amino acid)$_{n+1}$-DNR in DMF (50 ml per mmole DNR). After stirring for 5 min at RT, the mixture $Et_2O$:N-hexane (1:1, 6 ml per mmole DNR) was added. The precipitate was filtered in a glass fit, thoroughly washed with the same mixture and dissolved in chloroform (6 ml per mmole DNR). The product was purified by silica gel column (mobile phase chloroform=MeOH, <10%), the solvent evaporated and its purity assessed by HPLC (See General Methods, Section D.1.).
  The residue was either used, without further purification, for further synthesis with Fmoc-protected amino acids or was dissolved in water by adding HCl dropwise (0.1M water solution), pH controlled (>4.0) and lyophilized.

B. TLC Method for Qualitative Analysis of DNR/DOX Peptidic Derivatives
  TLC analysis was carried out on silica gel 60F-254 nm-0.25 mm plates (Merck) with DCM:MeOH:$H_2O$:Formic acid 88% (85:15:1:2, v/v) for elution.

C. HPLC Method #1 for Purity Analysis of Fmoc-Containing Peptidic Derivatives of DNR and DOX
  The column was TSK Gel Super ODS (ref. 18197, 2 µm). Solvent A was TFA 0.1% in water (w/v), and Solvent B was TFA 0.1% in ACN (v/v).
  Method: 30-36% of Solvent B in 2 min, 36-41% of Solvent B in 10 min, 41-90% of Solvent B in 3 min, 5 min at 90% Solvent B. Flow rate of 1.000 ml/min. UV detection at 254 nm. Fluorescence detection with ex. λ of 480 and em. λ of 560 nm. Purity of the compounds was assessed as the percentage surface area of the peaks.

D. HPLC Method #2 for Purity Analysis of Peptidic Derivatives of DNR and DOX
  1. DNR
  The column was Luna C18 3 µm, 4.6×100 mm ID (ref. 00d-4251-e0). Solvent A was TFA 0.1% in water (w/v), and Solvent B was TFA 0.1% in ACN (v/v).
  Method: 31% of Solvent B for 5 min, 31-43% of Solvent B in 3 min, 43-90% of Solvent B in 0.5 min, 2.5 min at 90% Solvent B. Flow rate of 1.500 ml/min. UV detection at 254 nm. Fluorescence detection with ex. λ of 480 and em. λ of 560 nm. Purity of the compounds was assessed as the percentage surface area of the peaks.

2. DOX

The column was Symmetry shield waters RP8 3.5 µm, 4.6×150 mm ID (Part AWT094269). Solvent A was 80% formate ammonium in water (w/v) 20 mM pH4.5+20% acetonitrile (v/v), and Solvent B was 20% formate ammonium in water (w/v) 20 mM pH4.5+80% ACN (v/v).

Method: Column is equilibrated with solvent A for 7 min. Gradient of 100% Solvent A to 100% solvent B in 30 min. Flow rate of 1.000 ml/min. UV detection at 254 nm. Fluorescence detection with ex. λ of 480 and em. λ of 560 nm. Purity of the compounds was assessed as the percentage surface area of the peaks.

E. Cultured Cells

MCF-7/6 cultured cells were graciously provided by Professor M. Mareel from the Ghent University (Belgium).

The B16-B16 cell line was obtained from the ATCC.

LS-174-T, the trypsinized variant of LS-180 (CL-187) colon adenocarcinoma line, was obtained from ATCC (CL 188)

F. Culture Medium and Routine Cell Culture

DMEM-F12 (Gibco) culture medium was used for all types of cultured cells. It was completed with 10% BFS (Gibco). A so-called "defined" culture medium was used for the preparation of the cell-conditioned medium.

1. Serum-Containing Medium

Serum-containing medium was generally composed of a basic culture medium completed with 10% inactivated BFS. Inactivation was accomplished by incubating the serum at 56° C. for 30 min in a water bath. L-Glutamine (2 mM) was also added. Some culture media already contained a stable form of the L-glutamine equivalent, called glutamax. 100 IU/ml of penicillin and 0.1 mg/ml of streptomycin could also be added to the cultured cells to avoid bacterial contamination.

2. Defined Medium

The medium was prepared with DMEM-F12 without phenol red, and completed with the following products: 10 µg/ml human apotransferrin, 200 µg/ml BSA, 1 µg/ml insulin and 10 nM of 17-β-estradiol.

No serum was added to the medium.

3. Routine Cell Culture

All cell types were commonly cultured in sterile TC/PS flasks, maintained in a standard incubator at 37° C. (95% $O_2$ and 5% $CO_2$). The culture medium was changed every 2-3 days.

Confluent cells were harvested for transfer into new flasks. This was done by rinsing the confluent cell layer with PBS containing 0.53 mM EDTA, completed with 0.25% trypsin. When harvested (from 5-10 min of incubation with the trypsin-containing solution), the cells were suspended in a fresh serum-containing culture medium and centrifuged at 300 g for 10 min. The pellet was resuspended in fresh medium and distributed into new flasks.

G. Preparation of Medium Conditioned by MCF-7/6 Cancer Cells ("CM")

MCF 7/6 cells were grown until subconfluence (not entirely continuous cell layer) in complete medium in 175 cm² TC/PS flasks. The cells were then washed with PBS (3×), 15 ml of defined medium was added to each flask, and the cells incubated for 24 hr at standard conditions.

The preparation of the CM, concentrated 20× was as follows. The medium was recovered, cooled down to 4° C. and centrifuged at 300×g for 10 min to remove suspended cells. The medium was then concentrated 20× using an Amicon concentrator (Millipore) containing membranes with a cut off at 10 kDa (YM10-Millipore).

H. Preparation of Drug Solutions

Compounds to be tested in biological experiments (stability, uptake, cytotoxicity tests or in vitro injections) were dissolved in water (1/10 of the expected volume) and further diluted with 0.9% (w/v) NaCl. The concentration of these solutions was checked ($A_{475nm}$ determination for anthracyclines) after sterilization by filtration (0.22 µm) and adjusted to the final required value using sterile 0.9% (w/v) NaCl.

I. Test of Stability of Oligopeptidic Derivatives of Anthracyclines in Blood and Conditioned Medium Compounds were mixed with fresh blood of healthy volunteers collected in heparinized tubes or CM (4° C., ice water bath) to obtain the desired final dilution. Compounds were extracted immediately after being mixed in (time 0) as well as after desired intervals of incubation (37° C., ice water bath).

1. Incubation (Example)

810 µl of blood+90 µl of the compound tested at 172.4 µM or 540 µM of CM (concentrated 20×)+60 µl of the compound at 172.4 µM were mixed in Eppendorf tubes. CM (20×) was made 10% (v/v) of phosphate buffer (1M pH 7.4) before use.

2. Extraction (Example)

In glass tubes of 10 ml was mixed 1.8 ml of chloroform: MeOH (4:1, v/v). Compounds in which the amino group was replaced by a free carboxy group (succinylated prodrugs for example) were extracted with 600 µl of citric buffer (citric acid 0.5M water solution, pH adjusted to 3.5 with NaOH). Compounds were extracted immediately as well as after desired periods of incubation (3×25 µl). The sample (500 µl) and 100 µl of the internal standard at 3.5 µM were added to the mixture (commonly DOX-HCl for DNR derivatives and L-prolyl-DNR for DOX derivatives). 600 µl of borate buffer (0.5M pH 9.8) was added and immediately vortexed. The tubes were centrifuged at 1500 g for 5 min. The organic phase (1 ml) was recovered in glass tubes and dried under nitrogen flow. A mixture of TFA 0.1% in $H_2O$ (70%, v/v) and TFA 0.1% in ACN (30%, v/v) was added to each tube (500 µl). The compounds were dissolved by ultrasonication for 15 sec between (100 W). The solution was recovered and filtrated (0.22 µm filters) for HPLC analysis (See General Methods, Section J.).

J. HPLC Method #3 for Analysis of DNR and its Peptidic Derivatives During Experiments In Vitro The column was TSK Gel Super ODS (ref 18197, 2 µm). Solvent A was TFA 0.1% in water (w/v), and Solvent B was TFA 0.1% in ACN (v/v).

Method: 30% of Solvent B (v/v) for 6.5 min, 30-90% of Solvent B (v/v) in 1 min, 2 min at 90% Solvent B. Flow rate of 1.500 ml/min. UV detection at 254 nm. Fluorescence detection with ex. λ of 480 and em. λ of 560 nm. Purity of the compounds was assessed as the percentage surface area of the peaks.

K. Synthesis of Fmoc-Protected Oligopeptides by the Merrifield SPPS Method

The Merrifield SPPS method is described in The Chemistry of Polypeptides, P. G. Katsoyannis Ed., Plenum Press, New-York, pp. 336-361, 1973. This method includes three major steps and is shown in Schemes I and II. The completeness of the reaction was measured by the ninhydrin test, as described above in Scheme I.

L. HPLC Method #4 for Analysis of Fmoc-Containing Oligopeptides

The column was TSK Gel Super ODS (ref. 18197, 2 µm). Solvent A was TFA 0.1% in water (w/v), and Solvent B was TFA 0.1% in ACN (v/v).

Method: 0-70% of Solvent B in 30 min. Flow rate of 1.200 ml/min. UV detection at 254 nm. Fluorescence detection with ex. λ of 480 and em. λ of 560 nm. Purity of the compounds was assessed as the percentage surface area of the peaks.

Sample preparation was as follows. Peptide samples for HPLC were prepared by dissolving the products in acetic acid (96%, v/v) or MeOH (+t° C.) at approximately 10 mg/ml and filtered on a 0.22 µm filter. Not more than 10 µl of such sample was then injected for analysis.

M. Synthesis of Peptidic Compounds by Coupling of Fmoc-Protected Oligopeptides to Anthracyclines 1. Products DOX-HCl; DNR-HCl; L-Leu-DOX-HCl; L-Leu-DNR-HCl; Fmoc-D-Ala-Leu-Lys(Fmoc)-Leu-OH SPPS (See General Methods, Section K); HATU; DIPEA; DMF; apyrogen water; lactate buffer; piperidine; CDM (analytical reagent, Labscan); chloroform; sodium sulfate; MeOH; $Et_2O$; N-hexane; EtOH (for synthesis, Merck); formic acid (GR, Merck); ACN (analytical reagent, Labscan); TFA (free acid, Sigma); C18 ODS-A silica gel (40-60 µm, 120 Å, YMC).

2. Synthesis of $(Fmoc)_n$-Peptide-Anthracycline

Anthracycline-HCl (1.0 eq.) and the Fmoc-protected peptide (1.2 eq.) were dissolved in DMF (50 ml per mmole of anthracycline). After addition of DIPEA (2.0 eq.), the mixture is stirred for 15 min at RT (in the dark). A solution of HATU (1.1 eq.) in DMF (20 ml per mmole of anthracycline) was added. After the mixture was stirred for 2 hours, cold water (4° C., 135 ml per mmole of anthracycline) was added and stirred an additional 30 min. The precipitate was filtered on qualitative paper (Whatman 1), washed with water (20 ml per mmole DNR), 2% lactate buffer (pH 4, 2×30 ml per mmole DNR), then water (2×30 ml per mmole DNR). The solid was dissolved in water and lyophilized to give Fmoc-peptide-anthracycline. Purity was assessed by TLC (See General Methods, Section B.) and HPLC (See General Methods, Section C.).

3. Synthesis of Peptide-Anthracycline Lactate

Piperidine (50.0 eq. per Fmoc-group) was added to a solution of $Fmoc_n$-anthracycline in DMF (50 ml per mmole DNR). After stirring for 5 min at RT, the reaction mixture was cooled (ice salt bath) and pre-cooled (4° C.), 10% lactate buffer pH 3.0 was added. The aqueous solution was extracted with DCM (3×100 ml per ml mmole anthracycline) and purified by solid phase extraction (YMC gel, 25 g per mmole of anthracycline). The MeOH was removed and the residue was dissolved in water and lyophilized to give peptide-anthracycline lactate. Its purity was assessed by HPLC (See General Methods, Section D.1. or D.2.).

N. Plasmin Assay

This assay is based on the proteolytical cleavage of D-Ala-Leu-Lys-7-amido-4-methylcoumarin by plasmin with restitution of a fluorogenic compound.

Materials: D-Ala-Leu-Lys-7-amido-4-methylcoumarin (Sigma), 2 mM stock solution in DMF, as substrate; TES buffer; control enzyme solution (Sigma) or sample; PBS; and 7-amido-4-methylcoumarin (Sigma).

In an eppendorf tube, 50 µl of the substrate at a concentration of 50 µM in DMF were mixed with 900 µl of TES buffer and 50 µl of an enzyme-containing solution. The mixture was incubated for 1 hour at 25° C. Fluorescence was determined ($\lambda_{exc}$=350 nm, $\lambda_{em}$=496 nm; fluorometer standardized with a 10 nM solution of 7-amido-4-methylcoumarin in PBS and the whole mixture excluding the enzyme). A dosage curve was done in parallel with known plasmin concentrations (at least five ½ dilutions). Plasmin activity was determined and expressed in IU/ml; µmole substrate transformed/min×ml.

O. Chemotherapy Studies (General Procedure)

Animals were kept under pathogen-free conditions with food and water supplied ad libitum, and kept for about one week before implantation of the tumors. Fragments (~2 mm) of tumors grown in nude mice were implanted subcutaneously in both flanks of the mice. Tumors were generally allowed to grow to attain a diameter of 5-6 mm each (approximately two weeks).

The mice weighed 20.0-25.0 g at the beginning of the study. They were selected and assigned to groups in order to have equally distributed tumor volumes in the different groups. In each group, mice were labeled individually. Treatments were assigned randomly to those groups.

All dosing solutions were prepared the day of injection by dissolution in water (1/10 of the expected final volume) and further dilution with 0.9% (w/v) NaCl. The concentration of these solutions was checked ($A_{475\ nm}$ determination) after sterilization by filtration (0.22 µm) and adjusted to the final required value using sterile 0.9% (w/v) NaCl.

Treatments were administered by the i.p. route. The mice received a constant volume (10 µl/g) of either saline (control group) or drug. Mortality and clinical signs were recorded up to 4 hours post-treatment on dosing days, and daily thereafter. Their behavior was equally noted. Individual body weights were generally recorded daily until day 14 and at least twice a week thereafter.

Tumor growth was monitored by two-dimensional measurements using calipers and a precision of 0.5 mm. Tumor volumes were calculated according to the following formula:

$$V_t = [length \times (width)^2]/2$$

Median relative tumor volumes (RTV) were calculated as tumor volumes determined at individual days divided by tumor volumes on day 0. For treated groups, growth inhibition was estimated as the percentage ratio of median RTV of treated (T) mice versus controls (C) on each day of tumor treatment.

$$T/C(\%) = [Median\ RTV(treated\ group)/Median\ RTV\ (control\ group)] \times 100$$

The minimal T/C value (%) for each treatment was used as a parameter for maximum efficacy. Duration of growth inhibition was assessed by considering growth delays (T-C) for one (200%) and two (400%) doublings of the median RTV).

To determine the statistical significance of any difference in median RTV between two groups, the Mann-Whitney test was used. The test was conducted at a p level of 0.05 (two tailed) using the GraphPad Prism 3.00 software.

P. Lethality Studies (General Procedure)

The percentage of surviving mice and the mean body weight of each dose group was plotted as a function of time. Cumulative mortality on day 14 and day 28 was also plotted as a function of the dose level for the purpose of $IC_{50}$ determination. $IC_{50}$ values were determined from sigmoidal regressions performed with the GraphPad Prism 3.00 software.

Example 1

Synthesis of DNR and DOX Prodrugs

D-Ala-Leu-Lys-Leu-DNR (Compound I, DNR; SEQ ID NO:5) and D-Ala-Leu-Lys-Leu-Leu-DNR (Compound II, DNR; SEQ ID NO:6) were synthesized by covalent coupling of the protected peptide on the anthracyclines or on their L-Leucyl derivatives.

Compound I was synthesized by linking the peptide D-Ala-Leu-Lys-Leu to DNR. The Fmoc-protected tetrapeptide Fmoc-D-Ala-Leu-Lys(Fmoc)-Leu-OH was produced by SPPS using Boc-Leu-Merrifield resin, N-α-Boc-N-ε-Fmoc-Lys-OH ("Boc-Lys(Fmoc)-OH"), N-α-Boc-Leu-OH ("Boc-Leu-OH") and N-α-Fmoc-D-Ala-OH ("Fmoc-D-Ala-OH"), with DCC as the coupling agent (See Scheme I).

The Fmoc-protected peptide was then coupled to the amino-group of DOX or DNR or of their L-Leucyl derivative using HATU as the coupling agent and piperidine for Fmoc deprotection (See Scheme II).

Progress of the coupling and deprotection reactions was followed by TLC ($CHCl_3:CH_3OH:H_2O$; 120:20:1 by volume) and HPLC (See General Methods, Section C.). The final products were analyzed by mass spectrometry and HPLC (See General Methods, Section D.), electrospray and NMR. Details of the general procedure of the peptide synthesis are given above in reference to Schemes I and II. The HPLC method adapted for analysis of Fmoc-containing oligopeptides is described in General Methods, Section L.

Following these methods, similar compounds were synthesized using the anthracycline, DOX: D-Ala-Leu-Lys-Leu-DOX (Compound I, DOX) and D-Ala-Leu-Lys-Leu-Leu-DOX (Compound II, DOX).

The use of Fmoc for the protection of the amino groups of D-alanine and L-lysine assured an excellent stability of the growing peptide during Boc-deprotection and final cleavage of the peptide from the resin. At the same time, both of these protecting groups were easily removed with a one-step deprotection by piperidine (100 eq.). This simple approach allowed for synthesis of all designed compounds in only two steps with fairly good yields. The use of a unique batch of tetrapeptide D-Ala-Leu-Lys-Leu-OH for synthesis of four compounds assured the production of a homogeneous material for subsequent in vitro and in vivo experiments. Final purity of the synthesized compounds ranged from 90-97% according to HPLC analysis and was considered acceptable for in vitro and in vivo tests. Analytical results confirmed the expected molecular masses and structures.

Example 2

Plasmin Activity in Human Blood and Blood Stability of Compounds I, DNR and II, DNR Determination of plasmin activity was done as described in General Methods, Section N. A solution of D-Ala-Leu-Lys-7-amido-4-methylcoumarin was mixed with human blood to the final concentration of 5 µM and incubated at 37° C. for 15 min and the supernatant taken for analysis. Blood in the control solution was replaced by water. Solutions of Compounds I, DNR and II, DNR in water (17.24 mM) were added to the freshly collected (on citrate) whole human blood from healthy donors (final concentration; 0.06 mM for Compound I, DNR; 0.18 mM for Compound II, DNR) and incubated at 37° C. The compounds were extracted and HPLC samples prepared as described in General Methods, Section I. DOX was used as the internal standard. The samples were analyzed by the HPLC method described in General Methods, Section J.

No traces of plasmin-like activity were discovered in human blood with the synthetic substrate, D-Ala-Leu-Lys-7-amido-4-methylcoumarin. Values obtained after 1 hour with incubation of substrate dilution with blood at 37° C. did not differ from those obtained for the negative control solution.

Compound I, DNR (0.06 mM) remained perfectly stable in vitro, after incubation with human blood for 1 hour. Small peaks of products resulting from a non-specific degradation of the compound (called "aglycones" and not quantified) were observed after 8 hours. No anthracycline derivatives were liberated from the compound during this incubation time.

Compound II, DNR (0.18 mM) exhibited excellent stability in vitro, in the presence of human blood, with ±5.0% of L-Leu-DNR liberated after 24 hours.

Both compounds showed an excellent stability in human blood during the incubation at 37° C. A small quantity of degradation products after 1 hour of incubation were not due to the action of plasmin. After 24 hours of incubation of Compound II, DNR, only 5% of the incubation mixture was composed of L-Leu-DNR. These results correspond to those obtained with D-Ala-Leu-Lys-7-amido-4-methylcoumarin. This synthetic substrate of plasmin remained entirely stable during 1 hour of incubation at 37° C.

Example 3

Hydrolysis of Compounds I, DNR and II, DNR by Human Plasmin

Compounds I, DNR and II, DNR (0.17 mM), as well as D-Ala-Leu-Lys-7-amido-4-methylcoumarin (0.17 mM) were incubated at 25° C. in the presence of 0.1 units of human plasmin in a 50 mM, pH 8.0 TES buffer. For Compounds I, DNR and II, DNR, HPLC samples were prepared and analyzed by HPLC (See General Methods, Section J). In case of D-Ala-Leu-Lys-7-amido-4-methylcoumarin, after 1 hour of incubation, the fluorescence of the resulting solution was determined at $\lambda_{exc}$=350 nm, $\lambda_{em}$=496 nm (See General Methods, Section N.).

Compound II, DNR (0.05 mM) was incubated at 25° C. in the presence of 0.01, 0.05 or 0.1 units of human plasmin in a 50 mM, pH 8.0 TES buffer. After 15, 45 and 60 min of incubation, triplicate aliquots were removed and the drugs and metabolites extracted prior to HPLC analysis (See General Methods, Section J.).

Compounds I, DNR and II, DNR (17.24 µM) were incubated in a medium freshly conditioned by the cultured B16-B16 cells (20 times concentrated) for 2 hours at 37° C. After that time, triplicate aliquots were removed and the drugs and metabolites extracted prior to HPLC analysis (See General Methods, Section J.).

The results indicated that Compound I, DNR was relatively weakly hydrolyzed in vitro by human plasmin (approximately 2.75 nmol/min/unit). At the same time, the in vitro hydrolysis of Compound II, DNR was at least 10 times more rapid (27.90 nmol/min/unit). Enzymatic hydrolysis of D-Ala-Leu-Lys-7-amido-4-methylcoumarin monitored by 7-amido-4-methylcoumarin liberation under the same conditions gave a value of 20.40 nmol/min/unit.

Hydrolysis rate was found to be directly proportional to time and enzyme concentration with all plasmin dilutions. No hydrolysis of any of the compounds in the medium conditioned by B16-B16 cells was observed. Only small quantities of products resulting from a non-specific degradation were observed.

The results confirmed the role of an amino acid spacer in the efficient hydrolysis of amino acid derivatives of anthracyclines by plasmin. The kinetics of hydrolysis were shown to be linear and concentration-dependent. Negative results with the medium conditioned by B16-B16 cells obtained with 7-amido-4-methylcoumarin and Compounds I, DNR and II, DNR, indicate the absence of important plasmin-like activity in it, which can possibly be attributed to a cell surface-associated plasmin formation or to the absence of specific conditions for plasminogen activation in vitro.

Example 4

In Vitro Accumulation by Cultured Tumor Cells

Compound I, DNR was incubated in vitro at 37° C. in the presence of MCF-7/6 human mammary carcinoma cells and the intracellular accumulation of the compound or its potential metabolites were analyzed by HPLC and fluorimetry, after extraction of the drugs from the cells.

Compound I, DNR was dissolved in distilled water at 17.24 µmole/ml and then diluted to obtain 0.02 mM in DMEM-F12 culture medium supplemented with 10% fetal calf serum (glutamax-I). Four ml of medium was poured in 25 cm² flasks (ref 3014. FALCON), and the cells were incubated for 30 minutes, 1, 3, 6 and 24 hours at 37° C. Then the cells were washed three times with PBS, and the cells were scraped from the flasks, and sonicated for 30 seconds at 100 Watts in a ice bath. Aliquots of 500 µl from each sample were then extracted with 1.8 ml of a chloroform:methanol mixture (4:1 by volume) to which 0.1 ml of 0.2 M borate buffer at pH 9.2, containing DOX at 3.4 mmole/ml as internal standard, were added. After stirring, the organic layer was dried and resuspended in 400 µl of distilled water, sonicated 5 minutes at 100 Watts in a ice-bath and filtered through a 0.22 µm filter (Waters-Millipore, MILLEX-GV) and then analyzed by HPLC.

On a aliquot of 100 µl, the protein content of the cell homogenate was determined. The results indicated that the accumulation of Compound I, DNR by cultured MCF-7/6 mammary carcinoma cells after 24 hours was extremely weak, representing approximately 0.1 µg/mg of cell proteins.

Example 5

Uptake of N-Leu-Leu-DNR and Compounds I, DNR and II, DNR by B16-B16 Cells

This experiment was conducted to evaluate whether the prodrugs were able to enter cultured cells in their non-hydrolyzed forms. In addition, it was desired to estimate the capacity of the prodrugs to induce detectable levels of products of their enzymatic hydrolysis (DNR and its amino acid derivatives) inside B16-B16 cells. N-Leu-Leu-DNR was chosen as a reference drug since it is the product that is directly liberated by plasmin from Compound II, DNR.

Confluent B16-B16 melanoma cell cultures were incubated in the presence of 17.24 µM dilutions in the serum-containing DMEM-F12 medium of either Compound I, DNR, Compound II, DNR, or N-Leu-Leu-DNR. At determined time points (1, 3, 5 and 24 hours), the cells were washed, harvested and lysed by ultrasonication. The concentration of the drugs and metabolites in the cell lysates were determined after extraction and HPLC analysis (See General Methods, Section J.). The amounts of anthracycline derivatives found per mg of protein were then compared.

The intracellular level of N-Leu-Leu-DNR after 3 hours of incubation with 17.73 µM of N-Leu-Leu-DNR was 7.74±0.75 nmol/mg cell protein, that of DNR was 0.67±0.12 nmol/mg cell protein, and that of L-Leu-DNR was 81.22±6.66 nmol/mg cell protein. After 24 hours, DNR attained 1.60±0.77 nmol/mg cell protein, L-Leu-DNR attained 1.04±0.10 mmol/mg cell protein, and L-Leu-Leu-DNR attained 98.57±16.76 nmol/mg cell protein.

In the case of Compound I, DNR, three major derivatives were present intracellularly at every point of incubation. A low level of non-hydrolyzed prodrug was detected. It grew up to three hours of incubation and remained stable afterwards. Its level was situated at 0.26±0.02 nmol/mg cell protein after 24 hours. On the other hand, the quantity of L-Leu-DNR continued to rise over a 24 hour period, to an intracellular level of 0.53±0.03 nmol/mg cell protein. DNR began to appear from the first hour (0.015±0.002 mmol/mg cell protein) to attain the level of 0.023±0.002 nmol/mg cell protein.

The level of Compound II, DNR detected did not considerably change in time and had the approximate value of 0.3 nmol/mg cell protein (starting from the first hour of incubation). A major metabolite found was L-Leu-DNR with quantities rising constantly during the study. The final quantity of this compound was 12.30±0.67 nmol/mg cell protein. Small quantities of DNR were also detected. Their level was 0.34±0.01 nmol/mg cell protein after 5 hours and 0.56±0.06 nmol/mg cell protein at the end of the incubation.

The absence of uptake of the non-hydrolyzed Compounds I, DNR and II, DNR is extremely important, along with their blood stability and sensitivity to plasmin action. The combination of these three properties allows these prodrugs to be classified as potential extracellularly tumor activated pro drugs.

Comparison of the kinetics of appearance of L-Leu-DNR and DNR during incubation of the tetra- and pentapeptidic derivatives with B16-B16 cells showed L-Leu-DNR being the major product and DNR displaying quite small and very slowly increasing quantities. At the same time, the level of L-Leu-DNR by Compound II, DNR was much higher as compared with Compound I, DNR (45.1-fold higher after 5 and 23.4-fold after 24 hours of incubation). No traces of N-Leu-Leu-DNR were found inside cells incubated in the presence of the pentapeptidic compound.

The absence of hydrolysis of Compound II, DNR in the medium conditioned by B16-B16 could be explained by the localization of plasmin-like activities on the cellular surface.

The pentapeptidic prodrug was shown to be more efficient that its tetrapeptidic counterpart in inducing intracellular L-Leu-DNR. This data confirmed the previously observed better enzymatic activation by Compound II, DNR in vitro.

Example 6

Acute Toxicity of Compound II, DOX in OF-1 Mice

Compound II, DOX was compared with DOX for determining its acute toxicity in OF-1 mice after intraperitoneal (i.p.) injection.

Male OF-1 mice (5 weeks old upon delivery), were kept for one week under laboratory conditions before the experiment. The body weight of the animals was approximately 30-35 g at the beginning of the test. The animals were divided in six groups (5 mice per group) for toxicity studies and marked individually. Each group received five i.p. injections of respectively 0.9% (w/v) NaCl (control group), or Compound II, DOX at 17.24, 25.86, 34.48, 43.1 and 60.34 µmol/kg on days 0-4.

Mortality and clinical signs were recorded up to 4 hours post-treatment on dosing days, and daily thereafter. Individual body weights were recorded daily until day 14 and at least twice a week thereafter. The percentage of surviving mice and the mean body weight of each dose group were plotted as a function of time. Cumulative mortality on day 14 and day 28 was also plotted as a function of the dose level for the purpose of $LD_{50}$ determination. $LD_{50}$ values were determined by regression analysis.

All animals survived to day 7. No lethality at all was observed in the control group of animals to the end. In terms of body weight, the control animals grew to reach a mean of 119.1% on day 35 (compared with day 0). All animals remaining from groups having received Compound II, DOX at 25.86 µmol/kg.

Important body weight mean values changes were observed starting from the dose of 34.48 µmol/kg. All of these groups attained the critical threshold of 20% of loss as compared to the initial body weight. In the case of groups having received 43.1 and 60.34 µmol/kg, this arrived already after the first week of and for those with 34.48 µmol/kg, after the second one.

Clinical signs of toxicity observed for Compound II, DOX were the same as those caused by DOX: piloerection, tremor, motor disturbances, stupor and finally, paralysis of the hind legs. Appearance of all clinical signs correlated with the importance of the dose administered and served as negative prognostic factors to the survival of the animals.

The $LD_{50}$ value calculated on day 28 was 34.5 µmol/kg. The $LD_{50}$ value for DOX obtained under the same conditions was known to be 4.1 µmol/kg.

To be considered as a prodrug, a new compound should possess a decreased general toxicity. Thus, the expected $LD_{50}$ in a toxicity study should be higher for a conjugated drug as compared with the parent drug. Compound II, DOX has shown an $LD_{50}$ value 8.4-fold higher than that of DOX under the same conditions (34.5 as compared to 4.1 µmol/kg). The toxicity signs observed during this study with Compound II, DOX are characteristic of DOX, severe weight losses and neurotoxicity.

Example 7

Chemotherapeutic Activity of Compound II, DOX in the B16-B16 Murine Melanoma Model The mouse B16-B16 melanoma model was chosen for the first chemotherapy experiment with Compound II, DOX.

Male C57-B16 black mice were 5 weeks old upon delivery. The body weight of the animals was approximately 20 g at the beginning of the test (See General Methods, Section O).

The animals were divided in eight groups (5 mice per group). Confluent murine melanoma B16-B16 cells (See General Methods, Section E.) were washed twice with PBS and EDTA (See General Methods, Section F.) twice and detached with trypsin (2 min incubation at 37° C.), that was thereafter neutralized by DMEM-F12 (containing 10% of calf serum). The cells were centrifuged for 5 min at 300 g. The pellet was resuspended twice in the DMEM-F12 without serum and centrifuged 5 min at 300 g.

The number of cells per ml of DMEM-F12 was then estimated (Brucker chamber) and the dilution of $2.5 \times 10^5$ cells/ml prepared. Each animal received 200 µl of this suspension ($5.0 \times 10^4$ cells) in its tail vein. The day of injection was considered day 0 of the study. Each group received two i.p. injections of respectively 0.9% (w/v) NaCl (control group), DOX at 5.2 µmol/kg and at 8.6 µmol/kg, or Compound II, DOX at 34.5 µmol/kg and at 69.0 µmol/kg on days 1 and 3. Animals were weighed on days 0, 1, 3, 6, 8 and 14. Their behavior and eventual clinical signs were also noted. All animals were sacrificed on day 14 and autopsied.

The lung lobes were fixed in a Bouin's solution (picric acid: formaldehyde, 40%: acetic acid, 15:5:1, v/v). Every lobe immersed in the fixing solution in a Petri flask was uniformly lighted against an opaque black background. Pictures of the front and back side of every lobe were taken with the help of a light microscope, scanned and digitized. The relative surface occupied by B116-B16 colonies was then estimated with the Scion Image Program.

The individual mean values were analyzed with the Scheffe's F-test to evaluate the statistical significance of differences observed between the groups. Each drug-treated group was compared to the control group and DOX-treated groups were compared to Compound II, DOX-treated groups.

No important weight changes were observed during the first week of the experiment for either group. The control group had better values up to day 8 (with a maximum at day 6 situated at 106.3% of day 0). That dropped to 101.6% at the end of the study.

In the case of the group treated with DOX at 5.2 µmol/kg, this parameter did not change substantially during the experiment, with a slight increase at day 14 (104.7%). Such an increase was more important for the group treated with DOX at 8.6 µmol/kg with 110% of initial mean weight at the end. The group having received Compound II, DOX at 34.5 µmol/kg followed a positive evolution with 104.5% on day 14. The group treated with Compound II, DOX at 69.0 µmol/kg remained more or less stable, with a slight tendency to lose weight up to day 8 (92.3%) broken afterwards with an increase up to 98.7% at the end of the experiment.

Non-treated animals from the control group had, with no exception, large merging black spots on every lobe analyzed. The ratio of the surface occupied by B16-B16 colonies to the non-affected one varied largely from one animal to another with a mean value of 45.7±12.6%. It was similar for the group treated with 5.2 µmol/kg of DOX (44.0±6.3% of surface occupied by metastases). The value obtained for the group having received DOX at 8.6 µmol/kg was 23.4±5.7%.

Compound II, DOX at 34.5 µmol/kg had a significant influence on the spread of lung metastases with a decrease to 8.2±1.8% ($P<0.01$). The same prodrug at 69.0 µmol/kg provided 1.5%±0.6% of surface affected ($P<0.001$). It was noteworthy that there were still a large number of black spots scattered all over the lobe surface in this group. The difference was in the small size. The large size of metastases in the control group and the two groups treated with DOX and their subsequent merging did not permit any precise quantification of their number. In the case of animals treated with prodrugs, their number did not show any significant difference between the groups with values of approximately 800 per animal.

The study was designed to compare the chemotherapeutic efficacy of Compound II, DOX to that of DOX using a model involving a metastatic spread of cancer cells into the lungs. The B16-B16 murine melanoma model has the advantages of presenting the opportunity to quantify the metastatic progression, and the cells present a well-described implication of the plasminogen-plasmin system during their growth and metastasis.

In toxicity studies with high doses, weight loss is a direct consequence of drug toxicity. Chemotherapy experiments combine this factor with the negative influence of the cancer disease progress on the body weight and the eventual beneficial therapeutic activity realized with the drug being used.

The control group in this study had a tendency to lose weight (evolution from 106.3 to 101.6% of their initial value from day 6 to day 14). In the same period of time, groups treated with Compound II, DOX at 34.5 µmol/kg and at 69.0 µmol/kg gained 4.9 and 4.1%, respectively. This tendency observed in the control group may be attributed to the influence of the induced metastases on the experimental animals. results concerning the B16-B16 metastases in lungs of mice from this group confirm this conclusion with lungs severely affected (45.7±12.6% of the lung surface occupied with metastases).

Compound II, DOX gave excellent results in this experiment. Two groups of mice having received 34.5 µmol/kg and at 69.0 µmol/kg, respectively, did not show any important weight losses during the experiment. No clinical signs of toxicity were observed. At the same time, the drug had a marked effect on the metastatic growth. In the case of the dose of 34.5 µmol/kg, the drug had a beneficial effect compared to the control group with only 8.2±1.8% of the lung surface colonized (P<0.01). The drug given at 69.0 µmol/kg gave the value of 1.5±0.6%, that is 15.6 times lower than in the case of the highest DOX dose of 8.6 mmol/kg (P<0.001). DOX did not show any significant activity in either dose with, however, some tendency to decrease the surface of lung metastases at 8.6 µmol/kg (23.4±5.7% against 45.7±12.6% in the non-treated group).

Example 8

Chemotherapeutic Activity of Compound II DOX in the LS174T Human Colon Tumor Xenograft Model The in vivo efficacy of Compound II, DOX by the i.p. route in mice bearing LS174T colon tumor xenografts was studied. DOX was used as a control. These tumors are known to resist treatment with anthracyclines. Estimation of the antitumor activity of Compound II, DOX, when administered at equitoxic doses and in the same experimental model, is of crucial importance for validation of the prodrug and the concept of an extracellularly tumor activated prodrug.

Female Swiss nude mice were 5 weeks old upon delivery (See General Methods, Section O). They were kept under pathogen-free conditions with food and water supplied ad libitum, and kept for about one week before implantation of the tumors. Fragments (~2 mm) of LS174T tumors grown in nude mice were implanted subcutaneously in both flanks of the mice used in the study. Tumors were left to grow for 17 days. At that time, the mice weighed about 20.5-26.5 g.

Mice were then selected and assigned to groups in order to have equally distributed tumor volumes in different groups (5-6 mice, 9-10 tumors/group). The dose levels of Compound II, DOX used in the study, were selected on the basis of a lethality study previously conducted on OF-1 normal mice. The dose of DOX was based on previous chemotherapy experiments performed in nude mice with the same dosing schedule.

Treatments were administered by the i.p. route on days 0, 1, 2, 3 and 4, the mice receiving a constant volume (10 µl/g) of either saline or the different dosing solutions. DOX was used at 3.8 µmol/kg, Compound II, DOX was used at 25.9 µmol/kg and 34.5 µmol/kg. Clinical signs (recorded 0.5, 1, 2 and 4 hours after dosing and daily between dosing days) and body weights (recorded on each day of tumor measurement) were used to assess treatment toxicity, tumor growth was monitored on days 7, 12, 15, 19, 22, 26, 29, 33 and 36 by two-dimensional measurements using calipers and a precision of 0.5 mm.

No treatment-related mortality and no significant weight loss was observed in the control and DOX-treated groups, as well as in the groups that received the lower dosage of Compound II, DOX.

In the Compound II, DOX at 34.5 µmol/kg group, three mice died before the end of the study, on days 18, 34 and 35, respectively. The mean body weight in this group reached its maximum of 14% of loss on day 26. According to the Mann-Whitney test, Compound II, DOX is the only treatment that resulted in significant differences as compared to the control animals. Significant difference existed between the groups treated with this compound and the DOX-treated group.

The plasmin-targeted prodrug clearly showed activity, the most interesting results being obtained in Compound II, DOX at 34.5 µmol/kg with a minimal T/C ratio of 23% reached on day 33 and a specific growth delay (one doubling of tumor size) of 1.7. However, this dose was slightly toxic and higher than its maximum tolerated dose. It could be clearly seen however, that a therapeutic effect was observed with the 25.9 µmol/kg dosage. Indeed, at 22 days, a significant median RTV value reduction of 50% was observed. No tumor regression was observed in this study in any of the DOX treatment groups. Considering the total lack of activity of DOX in the same model, these results are promising.

All publications and patent applications mentioned in this specification are herein incorporated by reference to the same extent as if each individual publication or patent application was specifically and individually indicated to be incorporated by reference.

While the present invention has been described with reference to the specific embodiments thereof, it should be understood by those skilled in the art that various changes may be made and equivalents may be substituted without departing from the scope of the invention. In addition, many modifications may be made to adapt a particular situation, material, composition of matter, process, process step or steps, while remaining within the scope of the present invention. Accordingly, the scope of the invention should therefore be determined with reference to the appended claims, along with the full range of equivalents to which those claims are entitled.

What is claimed is:

1. A method for treating a patient having a medical condition associated with plasmin overproduction, the method comprising administering to the patient a compound comprising:
   (1) a therapeutic agent capable of entering a target cell;
   (2) an oligopeptide having the formula $(AA^x)_m$-$(AA^y)_n$ (SEQ ID NO: 1) wherein: $(AA^x)_m$ is a plasmin substrate and each $AA^x$ independently represents an amino acid selected from the group consisting of Leu, Lys, Val, Phe, Ala, Glu, Be, Gly, Pro and Arg; each $AA^y$ independently represents an amino acid selected from the group consisting of Ile, Leu, Phe and Val; m is an integer from 2-4; and n is an integer from 1-2;
   (3) a stabilizing group; and
   (4) optionally, a linker group not cleavable by plasmin;
   wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide;
   wherein the stabilizing group hinders cleavage of the oligopeptide by enzymes present in whole blood; and
   wherein the compound is cleaved by plasmin under physiological conditions.

2. The method of claim 1 wherein the compound is administered intravenously.

3. The method of claim 1 wherein the patient is treated for a medical condition selected from the group consisting of cancer, neoplastic diseases, tumors, inflammatory diseases, and infectious diseases.

4. A method for decreasing the toxicity of a therapeutic agent wherein the therapeutic agent is intended for administration to a patient having a medical condition associated with plasmin overproduction, the method comprising: covalently forming a prodrug by linking an oligopeptide cleavable by plasmin to a stabilizing group at a first attachment site of the oligopeptide and directly or indirectly linking the therapeutic agent at a second attachment site of the oligopeptide, wherein the oligopeptide has the formula $(AA^x)_m$-$(AA^y)_n$ (SEQ ID NO: 1) wherein: $(AA^x)_m$ is a plasmin substrate and each $AA^x$ independently represents an amino acid selected from the group consisting of Leu, Lys, Val, Phe, Ala, Glu, Ile, Gly, Pro and Arg; each $AA^y$ independently represents an amino acid selected from the group consisting of Ile, Leu, Phe and Val; m is an integer from 2-4; and n is an integer from 1-2, and wherein the compound is cleavable by plasmin, whereby the prodrug provides for decreased toxicity of the therapeutic agent when administered to the patient.

5. A compound comprising:
(1) a therapeutic agent capable of entering a target cell;
(2) an oligopeptide having the formula X-Y, where X is a plasmin peptide substrate of 2-4 amino acids independently selected from the group consisting of Leu, Lys, Val, Phe, Ala, Glu, Ile, Gly, Pro and Arg, and Y is a peptide comprising 1-2 amino acids independently selected from the group consisting of Ile, Leu, Phe and Val;
(3) a stabilizing group; and
(4) optionally, a linker group not cleavable by plasmin;
wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide;
wherein the stabilizing group hinders cleavage of the oligopeptide by enzymes present in whole blood; and
wherein the compound is cleavable by plasmin.

6. The compound of claim 5 wherein the target cell is a tumor or inflammatory cell.

7. The compound of claim 5 wherein plasmin is present in the extracellular vicinity of the target cell for the therapeutic agent.

8. The compound of claim 5 wherein plasmin cleaves the linkage between X and Y of the oligopeptide.

9. The compound of claim 5 which is selectively cleavable by plasmin.

10. The compound of claim 5 being a prodrug having an active portion, wherein the active portion of the prodrug is more capable of entering the target cell after cleavage by the plasmin than prior to cleavage by plasmin, the active portion including at least the therapeutic agent.

11. The compound of claim 10 wherein the active portion of the prodrug consists of the therapeutic agent.

12. The compound of claim 10 wherein the active portion of the prodrug includes the therapeutic agent and at least the linker group.

13. The compound of claim 10 wherein the active portion of the prodrug includes the therapeutic agent and one amino acid of the Y portion of the oligopeptide.

14. The compound of claim 13 further comprising two amino acids of the Y portion of the oligopeptide.

15. The compound of claim 5 wherein the oligopeptide is selected from: Leu-Lys-Leu- and Leu-Lys-Leu-Leu (SEQ ID NO: 4).

16. The compound of claim 5 wherein X is $(AA^x)_m$ and Y is $(AA^y)_n$ wherein: $(AA^x)_m$ is a plasmin substrate and each $AA^x$ independently represents an amino acid selected from the group consisting of Leu, Lys, Val, Phe, Ala, Glu, Ile, Gly, Pro and Arg; each $AA^y$ independently represents an amino acid selected from the group consisting of Ile, Leu, Phe and Val; m is an integer from 2-4; and n is an integer from 1-2.

17. The compound of claim 16 wherein $AA^{x4}$ is an amino acid residue selected from the group consisting of Ile and Phe.

18. The compound of claim 16 wherein $AA^{x3}$ is an amino acid residue selected from the group consisting of Ala, Glu, Gly, Ile, Leu, Phe, Pro and Val.

19. The compound of claim 16 wherein $AA^{x2}$ is an amino acid residue selected from the group consisting of Ala, Glu, Gly, Leu, Lys, Phe, Pro and Val.

20. The compound of claim 16 wherein $AA^{x1}$ is an amino acid residue selected from the group consisting of Arg and Lys.

21. The compound of claim 16 wherein $AA^{y2}$ and $AA^{y1}$ are amino acid residues selected from the group consisting of Ile, Leu, Phe and Val.

22. The compound of claim 16 wherein $AA^{y2}$ and $AA^{y1}$ are Leu residues.

23. The compound of claim 16 wherein $AA^{y1}$ is a Leu residue and $AA^{y2}$ is absent.

24. The compound of claim 5 wherein the stabilizing group is selected from the group consisting of D-Ala, β-Ala, α-methyl-Ala, Succ-D-Ala, Succ-β-Ala and Succ-α-methyl-Ala.

25. The compound of claim 5 wherein the therapeutic agent is selected from the group consisting of alkylating agents, anthracyclines, camptothecins, cyclosporins, dolastatins, enediynes, epipodophyllotoxins, maytansinoids, naphtalimides, pteridines, rhodamines, sulfoximines, taxanes, taxoids, and vinca alkaloids.

26. The compound of claim 5 wherein the therapeutic agent is selected from the group consisting of actinomycin D; alkylating agents; amiodarone; anthracyclines; AT-125 or activin ((αS,5S)-α-amino-3-chloro-4,5-dihydro-5-isoxazole acetic acid); bamipine; bleomycin; 5-bromodeoxyuridine; calicheamicin; camptothecins; L-canavanine; carboplatin; CC-1065; chlorphenoxamine; chloroquine; colchicine; combretastatin and combretastatin $A_4$ phosphate; coumarins; cyclophosphamide; cyclosporins; cytarabine; dehydrodidemnin B; dipyridamole; discodermolide; docetaxel; dolastatin 10, dolastatin 11 and dolastatin 15; duocarmycin; epothilone A; etoposide and etoposide phosphate; fludarabine; 5-fluorouracil; folic acid derivatives; KW-2189; 6-maytansinoids; mitomycin C; naphtalimides; nitrosoureas; paclitaxel; phenylenediamine mustards; cis-platin; podophyllotoxin and podophyllotoxin derivatives; porfiromycin; quinidine; quinine; reserpine; rhodamines; sulfoximines; tamoxifen; taxoids; topotecan; trifluoperazine; verapamil; vinca alkaloids; and derivatives and analogs thereof.

27. The compound of claim 5 wherein the therapeutic agent is daunorubicin.

28. The compound of claim 5 wherein the therapeutic agent is doxorubicin.

29. The compound of claim 5 wherein the therapeutic agent has an intracellular active site.

30. The compound of claim 5 wherein the oligopeptide is directly linked to the therapeutic agent.

31. The compound of claim 5 wherein the oligopeptide is indirectly linked to the therapeutic agent at the second attachment site of the oligopeptide via a linker group, and the linker group is selected from the group consisting of amino caproic acid, hydrazide group, an ester group, an ether group, and a sulphydryl group.

32. The compound of claim 5 wherein X is a plasmin peptide substrate of 2-4 amino acids independently selected from Leu-Lys, Val-Leu-Lys, Phe-Lys, Ala-Phe-Lys, Ala-Lys, Ala-Ala-Lys, Leu-Lys-Lys, Glu-Lys-Lys, Phe-Glu-Lys-Lys (SEQ ID NO: 2), Glu-Lys, Phe-Glu-Lys, Ile-Glu-Lys, Gly-Gly-Arg, Val-Gly-Arg, Ile-Glu-Gly-Arg (SEQ ID NO: 3), Pro-Arg, Gly-Pro-Arg, Phe-Val-Arg, Leu-Arg, Phe-Arg and Pro-Phe-Arg.

33. An oligopeptide having the formula $(AA^x)_m$-$(AA^y)_n$ (SEQ ID NO: 1) wherein: $(AA^x)_m$ is a plasmin substrate and each $AA^x$ independently represents an amino acid selected from the group consisting of Leu, Lys, Val, Phe, Ala, Glu, Ile, Gly, Pro and Arg; each $AA^x$ independently represents an amino acid selected from the group consisting of Ile, Leu, Phe and Val; m is an integer from 2-4; and n is an integer from 1-2, said oligopeptide being cleavable by plasmin, wherein the oligopeptide is linked to a therapeutic agent.

34. The oligopeptide of claim 33 wherein the oligopeptide is linked to a stabilizing group.

35. An oligopeptide having the formula $(AA^x)_m\text{-}(AA^y)_n$ (SEQ ID NO: 1) wherein: $(AA^x)_m$ is plasmin substrate and each $AA^x$ independently represents an amino acid selected from the group consisting of Leu, Lys, Val, Phe, Ala, Glu, Ile, Gly, Pro and Arg; each $AA^y$ independently represents an amino acid selected from the group consisting of Ile, Leu, Phe and Val; m is an integer from 2-4; and n is an integer from 1-2, said oligopeptide being cleavable by plasmin, wherein the oligopeptide is linked to a P-glycoprotein inhibitor.

36. An oligopeptide having the formula $(AA^x)_m\text{-}(AA^y)_n$ (SEQ ID NO: 1) wherein: $(AA^x)_m$ is a plasmin substrate and each $AA^x$ independently represents an amino acid selected from the group consisting of Leu, Lys, Val, Phe, Ala, Glu, Ile, Gly, Pro and Arg; each $AA^y$ independently represents an amino acid selected from the group consisting of Ile, Leu, Phe and Val; m is an integer from 2-4; and n is an integer from 1-2, said oligopeptide being cleavable by plasmin, wherein the oligopeptide is linked to a γ-glutamylcysteine synthetase inhibitor.

37. A pharmaceutical composition comprising:
(1) A compound comprising:
(a) a therapeutic agent capable of entering a target cell;
(b) an oligopeptide having the formula $(AA^x)_m\text{-}(AA^y)_n$ (SEQ ID NO: 1) wherein: $(AA^x)_m$ is a plasmin substrate and each $AA^x$ independently represents an amino acid selected from the group consisting of Leu, Lys, Val, Phe, Ala, Glu, Ile, Gly, Pro and Arg; each $AA^y$ independently represents an amino acid selected from the group consisting of Ile, Leu, Phe and Val; m is an integer from 2-4; and n is an integer from 1-2;
(c) a stabilizing group; and
(d) optionally, a linker group not cleavable by plasmin;
wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide;
wherein the stabilizing group hinders cleavage of the oligopeptide by enzymes present in whole blood; and
wherein the compound is cleaved by plasmin under physiological conditions; and
(2) a pharmaceutically acceptable carrier.

* * * * *